United States Patent
Shi et al.

(10) Patent No.: US 12,364,452 B2
(45) Date of Patent: Jul. 22, 2025

(54) DIAGNOSTIC INFORMATION PROCESSING METHOD AND APPARATUS BASED ON MEDICAL IMAGE, AND STORAGE MEDIUM

(71) Applicant: HANGZHOU YITU HEALTHCARE TECHNOLOGY CO., LTD., Hangzhou (CN)

(72) Inventors: Lei Shi, Hangzhou (CN); Xuan Zang, Hangzhou (CN); Jing Shi, Hangzhou (CN)

(*) Notice: Subject to any disclaimer, the term of this patent is extended or adjusted under 35 U.S.C. 154(b) by 335 days.

(21) Appl. No.: 17/760,185

(22) PCT Filed: Feb. 5, 2021

(86) PCT No.: PCT/CN2021/075379
§ 371 (c)(1),
(2) Date: Aug. 4, 2022

(87) PCT Pub. No.: WO2021/155829
PCT Pub. Date: Aug. 12, 2021

(65) Prior Publication Data
US 2023/0070249 A1    Mar. 9, 2023

(30) Foreign Application Priority Data

| Feb. 5, 2020 | (CN) | .......................... 202010081111.5 |
| Feb. 7, 2020 | (CN) | .......................... 202010083597.6 |
| Feb. 17, 2020 | (CN) | .......................... 202010096657.8 |

(51) Int. Cl.
*A61B 6/00* (2024.01)
*A61B 6/03* (2006.01)
(Continued)

(52) U.S. Cl.
CPC ............ *A61B 6/5217* (2013.01); *A61B 6/032* (2013.01); *G06T 7/0016* (2013.01); *G06T 7/11* (2017.01);
(Continued)

(58) Field of Classification Search
CPC ......... A61B 6/5217; A61B 6/032; G06T 7/62; G06T 7/11; G06T 7/0016; G06T 11/008;
(Continued)

(56) References Cited

U.S. PATENT DOCUMENTS

2018/0342060 A1* 11/2018 Yao .......................... G16H 40/20
2019/0209116 A1* 7/2019 Sjöstrand ............... G16H 50/30

* cited by examiner

*Primary Examiner* — Michael R Neff
(74) *Attorney, Agent, or Firm* — Novoclaims Patent Services LLC; Mei Lin Wong

(57) ABSTRACT

Disclosed are a diagnostic information processing method and apparatus based on a medical image, and a storage medium, to achieve disease grading based on a medical image. The method includes: acquiring a first lung medical image of a subject; acquiring image parameters of an affected area in the first lung medical image; and determining, according to the image parameters of the affected area, a disease grade of lungs of the subject corresponding to information of the first lung medical image. Using the solution provided by the present invention, the image parameters of the affected area in the first lung medical image can be acquired, and then the disease grade of the lungs of the subject corresponding to the information of the first lung medical image can be determined according to the image parameters of the affected area, so that a disease can be graded based on a medical image.

9 Claims, 14 Drawing Sheets

(51) Int. Cl.
*G06T 7/00* (2017.01)
*G06T 7/11* (2017.01)
*G06T 7/62* (2017.01)
*G06T 11/00* (2006.01)
*G06T 11/20* (2006.01)
*G16H 30/40* (2018.01)
*G16H 50/30* (2018.01)

(52) U.S. Cl.
CPC .............. *G06T 7/62* (2017.01); *G06T 11/008* (2013.01); *G06T 11/206* (2013.01); *G16H 30/40* (2018.01); *G16H 50/30* (2018.01); *G06T 2207/10081* (2013.01); *G06T 2207/20021* (2013.01); *G06T 2207/20084* (2013.01); *G06T 2207/30061* (2013.01)

(58) Field of Classification Search
CPC ......... G06T 11/206; G06T 2207/10081; G06T 2207/20021; G06T 2207/20084; G06T 2207/30061; G16H 50/30; G16H 30/40
USPC ........................................................ 382/128
See application file for complete search history.

DIAGNOSTIC INFORMATION PROCESSING METHOD AND APPARATUS BASED ON MEDICAL IMAGE, AND STORAGE MEDIUM

TECHNICAL FIELD

The present invention relates to the field of Internet technologies, and in particular, to a diagnostic information processing method and apparatus based on a medical image, and a storage medium.

BACKGROUND

At present, many lung diseases can be detected through CT images. However, at present, only a positive diagnosis can be made for diseases detected through CT images, but the severity of the diseases cannot be determined.

However, for some diseases, it is necessary to quickly obtain the severity of the diseases, and quickly formulate corresponding treatment plans for different grades of diseases. For example, novel coronavirus pneumonia, which spreads rapidly, requires early detection, early diagnosis, early isolation and early treatment. For such diseases, it is necessary to quickly determine the severity of such diseases, and then achieve disease grading. Therefore, how to provide a method for grading a disease based on a medical image is an urgent technical problem to be solved.

SUMMARY

The present invention provides a diagnostic information processing method based on a medical image, to achieve disease grading based on a medical image.

The present invention provides a diagnostic information processing method based on a medical image, including:

acquiring a first lung medical image of an examined object;

acquiring image parameters of an affected part in the first lung medical image; and determining, according to the image parameters of the affected part, a disease grade of lungs of the examined object corresponding to information of the first lung medical image.

The present invention has the following beneficial effects: the image parameters of the affected part in the first lung medical image can be acquired, and then the disease grade of the lungs of the examined object corresponding to the information of the first lung medical image can be determined according to the image parameters of the affected part, so that a disease can be graded based on a medical image.

In one embodiment, the acquiring image parameters of an affected part in the first lung medical image includes:

acquiring a normal CT value distribution interval in a lung and a CT value distribution interval of an affected part; and inputting at least one first lung medical image into a neuron network to determine a volume of the affected part in the first lung medical image.

In one embodiment, the neuron network includes:

a first detection model configured to detect a candidate patch shadow, a cutting model, a second detection model configured to detect a patch shadow interval, and a volume calculation model configured to calculate the volume of the affected part; and the inputting at least one first lung medical image into a neuron network to determine a volume of the affected part in the first lung medical image includes:

passing the at least one first lung medical image through N consecutive convolution feature extraction modules in the first detection model, so that the N consecutive convolution feature extraction modules obtain image features of a patch shadow in the first lung medical image, where N is a positive integer;

inputting image features of the affected part in the first lung medical image into a fully connected layer in the first detection model, so that the fully connected layer outputs the candidate patch shadow based on the image features;

passing the candidate patch shadow through the cutting model, so that the cutting model cuts the candidate patch shadow in different directions in space multiple times to obtain multiple section images of the candidate patch shadow in multiple directions in space;

passing multiple consecutive section images through M consecutive convolution feature extraction modules in the second detection model, so that the M consecutive convolution feature extraction modules obtain image features of the section images, where M is a positive integer;

inputting the image features of the section images into a fully connected layer in the second detection model, so that the fully connected layer outputs patch shadow information based on the image features; and passing the patch shadow information through the volume calculation model, so that the volume calculation model calculates the volume of the affected part in the first lung medical image.

This embodiments has the following beneficial effects: the neuron network formed by connecting multiple models can simultaneously realize patch shadow detection and volume calculation, thereby simplifying the method for determining the volume of the affected part.

In one embodiment, the determining, according to the image parameters of the affected part, a disease grade of lungs of the examined object corresponding to information of the first lung medical image includes:

comparing a volume of the affected part with a target relationship table, where the target relationship table stores a corresponding relationship between the volume of the affected part and the disease grade;

determining the disease grade of the lungs of the examined object according to a comparison result.

In one embodiment, the determining, according to the image parameters of the affected part, a disease grade of lungs of the examined object corresponding to information of the first lung medical image includes:

calculating a volume proportion of the affected part in the lungs; and inputting a volume of the affected part and the volume proportion of the affected part in the lungs into a disease grade calculation model, to obtain the disease grade of the lungs of the examined object that is comprehensively calculated by the disease grade calculation module based on the volume of the affected part and the volume proportion of the affected part in the lungs.

In one embodiment, the method further includes:

acquiring a second lung medical image of the examined object;

acquiring a volume of an affected part in the second lung medical image;

comparing the volume of the affected part in the second lung medical image with the volume of the affected part in the first lung medical image to determine a volume change trend of the affected part; and determining development trend information of a lung disease of the examined object according to the volume change trend of the affected part.

This embodiments has the following beneficial effects: the volume change trend of the affected part can be determined based on different lung medical images of the same examined object, so that the development trend information of a lung disease of the examined object is automatically determined through the volume change trend of the affected part.

In one embodiment, determining a development trend of the lung disease of the examined object according to the volume change trend of the affected part includes:

when the volume of the affected part conforms to a first trend, determining a first diagnostic result of the examined object; and when the volume of the affected part conforms to a second trend, determining a second diagnostic result of the examined object.

In one embodiment, the method further includes:

acquiring generation time of the first lung medical image and the second lung medical image; and calculating a disease development speed of the examined object according to the generation time and the volume change trend of the affected part.

In one embodiment, the method further includes:

rendering the first lung medical image based on a single color to generate a third lung medical image, where a color depth after rendering is positively correlated with a CT value; and/or rendering the first lung medical image based on multiple colors to generate a fourth lung medical image, where different CT values are rendered with different types of colors; and outputting the first lung medical image, the third lung medical image and/or the fourth lung medical image.

In one embodiment, the method further includes:

rendering multiple lung medical images with multiple colors, where portions of the rendered lung medical images having different CT values and/or CT value ranges correspond to different colors; and outputting multiple rendered lung medical images.

The present application further provides a method for displaying a diagnostic information interface, including:

forming a first graph based on first data, where the first graph is represented by a first color, and the first data is CT value density data of a region of interest in a first target CT image;

forming a second graph based on second data, where the second graph is represented by a second color; and determining an overlapping portion of the first graph and the second graph, and representing the overlapping portion by a third color, where the first graph and the second graph are used for representing the severity of a disease in the first target CT image.

In one embodiment, the forming a first graph based on first data includes:

determining the first data in response to acquiring the CT value density data of the region of interest in the first target CT image.

In one embodiment, the second data is benchmark data of a region of interest in a CT image.

In one embodiment, the second data is CT value density data of a region of interest in a second target CT image obtained at different time from the first target CT image.

In one embodiment, the region of interest includes at least one of the following regions:

human lung organ, left lung, right lung, superior lobe of right lung, middle lobe of right lung, inferior lobe of right lung, superior lobe of left lung, or inferior lobe of left lung.

In this embodiment, a diagnostic information interaction method based on a medical image is further provided, and includes:

acquiring a first lung medical image of an examined object;

acquiring image parameters of an affected part in the first lung medical image; and outputting, according to the image parameters of the affected part, a disease grade of lungs of the examined object corresponding to information of the first lung medical image.

The present application further provides a diagnostic information evaluation method based on a medical image, including:

partitioning a region of interest in a medical image to obtain at least N partitions, where N is a natural number greater than or equal to 2;

calculating at least a volume of a first sign and a volume proportion of a second sign in each partition;

acquiring score values corresponding to the volume proportions of the first sign and the second sign, and acquiring a score of each partition based on the score values; and evaluating the region of interest according to the score of each partition, where the evaluating the region of interest according to the score of each partition includes:

setting a corresponding score threshold, and then determining, based on the score threshold, the severity of a disease of an examined object corresponding to the medical image.

In one embodiment, the partitioning a region of interest in a medical image includes:

obtaining at least N partitions of the region of interest, where the region of interest is human lungs, and the N partitions are superior lobe of right lung, middle lobe of right lung, inferior lobe of right lung, superior lobe of left lung, and inferior lobe of left lung.

In one embodiment, the partitioning a region of interest in a medical image includes:

obtaining at least N partitions of the region of interest, where the region of interest is human lungs, and the N partitions are six partitions obtained by partitioning each of left and right lungs of the human lungs into three parts from top to bottom.

In one embodiment, the first sign is a patch region, and the second sign is a ground glass region.

In one embodiment, the acquiring score values corresponding to the volume proportions of the first sign and the second sign, and acquiring a score of each partition based on the score values includes:

obtaining a first product by multiplying a volume proportion score value of the first sign by a first parameter;

obtaining a second product by multiplying a volume proportion score value of the second sign by a second parameter; and determining that a sum value of the first product and the second product is a score value of partitions corresponding to the first sign and the second sign.

In one embodiment, the evaluating the region of interest according to the score of each partition includes:

setting first and second thresholds, where the second threshold is greater than the first threshold;

comparing the score with the first and second thresholds, respectively;

when the score is less than the first threshold, determining that the examined object corresponding to the medical image suffers from mild pneumonia;

when the score is greater than or equal to the first threshold and less than the second threshold, determining that the examined object corresponding to the medical image suffers from moderate pneumonia; and when the score is greater than or equal to the second threshold, determining that the examined object corresponding to the medical image suffers from severe pneumonia.

The present application further provides a diagnostic information evaluation method based on a medical image, including:

acquiring a first lung medical image of an examined object;

acquiring image parameters of an affected part in the first lung medical image; and outputting, according to the image parameters of the affected part, a disease grade of lungs of the examined object corresponding to information of the first lung medical image, where the outputting, according to the image parameters of the affected part, a disease grade of lungs of the examined object corresponding to information of the first lung medical image includes:

comparing a volume of the affected part with a target relationship table, where the target relationship table stores a corresponding relationship between the volume of the affected part and the disease grade;

determining and outputting the disease grade of the lungs of the examined object according to a comparison result;

or calculating a volume proportion of the affected part in the lungs; and inputting a volume of the affected part and the volume proportion of the affected part in the lungs into a disease grade calculation model, to obtain the disease grade of the lungs of the examined object that is comprehensively calculated by the disease grade calculation module based on the volume of the affected part and the volume proportion of the affected part in the lungs.

The present application further provides a diagnostic information display method based on a medical image, including:

displaying partitions of a medical image through a display interface; and outputting diagnostic information on the display interface in response to calculating image parameters of a first sign and a second sign in each partition, where the diagnostic information includes at least one of:

volume proportions of the first sign and the second sign, scores obtained based on volumes of the first sign and the second sign, or an evaluation result of the medical image obtained based on the scores.

The present invention provides a diagnostic information processing apparatus based on a medical image, including:

a first acquisition module, configured to acquire a first lung medical image of an examined object;

a second acquisition module, configured to acquire image parameters of an affected part in the first lung medical image; and a determination module, configured to determine, according to the image parameters of the affected part, a disease grade of lungs of the examined object corresponding to information of the first lung medical image.

In one embodiment, the second acquisition module includes:

an input submodule, configured to input at least one first lung medical image into a neuron network to determine a volume of the affected part in the first lung medical image.

In one embodiment, the neuron network includes:

a first detection model configured to detect a candidate patch shadow, a cutting model, a second detection model configured to detect a patch shadow interval, and a volume calculation model configured to calculate the volume of the affected part; and the input submodule is configured to:

pass the at least one first lung medical image through N consecutive convolution feature extraction modules in the first detection model, so that the N consecutive convolution feature extraction modules obtain image features of a patch shadow in the first lung medical image, where N is a positive integer;

input image features of the affected part in the first lung medical image into a fully connected layer in the first detection model, so that the fully connected layer outputs the candidate patch shadow based on the image features;

pass the candidate patch shadow through the cutting model, so that the cutting model cuts the candidate patch shadow in different directions in space multiple times to obtain multiple section images of the candidate patch shadow in multiple directions in space;

pass multiple consecutive section images through M consecutive convolution feature extraction modules in the second detection model, so that the M consecutive convolution feature extraction modules obtain image features of the section images, where M is a positive integer;

input the image features of the section images into a fully connected layer in the second detection model, so that the fully connected layer outputs patch shadow information based on the image features; and pass the patch shadow information through the volume calculation model, so that the volume calculation model calculates the volume of the affected part in the first lung medical image.

In one embodiment, the determination module includes:

a comparison submodule, configured to compare a volume of the affected part with a target relationship table, where the target relationship table stores a corresponding relationship between the volume of the affected part and the disease grade; and a first determination submodule, configured to determine the disease grade of the lungs of the examined object according to a comparison result.

In one embodiment, the determination module includes:

a calculation submodule, configured to calculate a volume proportion of the affected part in the lungs; and an input submodule, configured to input a volume of the affected part and the volume proportion of the affected part in the lungs into a disease grade calculation model, to obtain the disease grade of the lungs of the examined object that is comprehensively calculated by the disease grade calculation module based on the volume of the affected part and the volume proportion of the affected part in the lungs.

In one embodiment, the apparatus further includes:

a third acquisition module, configured to acquire a second lung medical image of the examined object;

a fourth acquisition module, configured to acquire a volume of an affected part in the second lung medical image;

a comparison module, configured to compare the volume of the affected part in the second lung medical image with the volume of the affected part in the first lung medical image to determine a volume change trend of the affected part; and a change trend determination module, configured to determine development trend information of a lung disease of the examined object according to the volume change trend of the affected part.

In one embodiment, the change trend determination module includes:

a second determination submodule, configured to determine, when the volume of the affected part conforms to a first trend, a first diagnostic result of the examined object; and a third determination submodule, configured to determine, when the volume of the affected part conforms to a second trend, a second diagnostic result of the examined object.

In one embodiment, the apparatus further includes:

a fifth acquisition module, configured to acquire generation time of the first lung medical image and the second lung medical image; and a calculation module, configured to calculate a disease development speed of the examined object according to the generation time and the volume change trend of the affected part.

In one embodiment, the apparatus further includes:

a first rendering module, configured to render the first lung medical image based on a single color to generate a third lung medical image, where a color depth after rendering is positively correlated with a CT value;

a second rendering module, configured to render the first lung medical image based on multiple colors to generate a fourth lung medical image, where different CT values are rendered with different types of colors; and a first output module, configured to output the first lung medical image, the third lung medical image and/or the fourth lung medical image.

In one embodiment, the apparatus further includes:

a third rendering module, configured to render multiple lung medical images with multiple colors, where portions of the rendered lung medical images having different CT values and/or CT value ranges correspond to different colors; and a second output module, configured to output multiple rendered lung medical images.

The present application further provides a non-transitory readable storage medium, where instructions in the storage medium, when executed by a processor in a device, enable the device to execute the method involved in any one of the foregoing embodiments.

Other features and advantages of the present invention are set forth in the following description, and some become apparent from the description or learned by practice of the present invention. The objectives and other advantages of the present invention may be realized and obtained through the structure particularly pointed out in the written description, claims, and drawings.

The technical solutions of the present invention are further described in detail below through the accompanying drawings and embodiments.

BRIEF DESCRIPTION OF THE DRAWINGS

The accompanying drawings are provided to further understand the present invention, and constitute a part of the description. The accompanying drawings, along with the embodiments of the present invention, are used to explain the present invention, and do not constitute a limitation to the present invention. In the accompanying drawings.

DETAILED DESCRIPTION

Various solutions and features of the present application are described herein with reference to the accompanying drawings.

It should be understood that various modifications may be made to the embodiments of the application herein. Therefore, the above-mentioned description should not be regarded as limiting, but merely as examples of the embodiments. Those skilled in the art will conceive of other modifications within the scope and spirit of the present application.

The accompanying drawings, which are included in and constitute part of the description, illustrate the embodiments of the present disclosure and, together with the general description of the present application given above and the detailed description of the embodiments given below, explain the principles of the present application.

These and other features of the present application will become apparent from the following description of preferred forms of the embodiments, given as non-limiting examples, with reference to the accompanying drawings.

It should also be understood that, although the present application has been described with reference to some specific examples, those skilled in the art may certainly implement many other equivalent forms of the present application, which have features as described in the claims and are therefore fall within the scope of protection defined thereby.

In conjunction with the accompanying drawings, the above and other aspects, features and advantages of the present application will become more apparent in view of the following detailed description.

The specific embodiments of the present application are described hereinafter with reference to the accompanying drawings; however, it should be understood that the claimed embodiments are merely examples of the present application, which may be implemented in various manners. Well-known and/or repeated functions and structures are not described in detail to avoid obscuring the present application with unnecessary or redundant details. Therefore, the specific structural and functional details claimed herein are not intended to be limiting, but merely serve as a basis for the claims and a representative basis for teaching those skilled in the art to use the present application in any substantially suitable detailed structure in many ways.

The description may use the phrases "in an embodiment", "in another embodiment", "in yet another embodiment" or "in other embodiments", which may all refer to one or more of the same or different embodiments according to the present application.

Figure 1A:
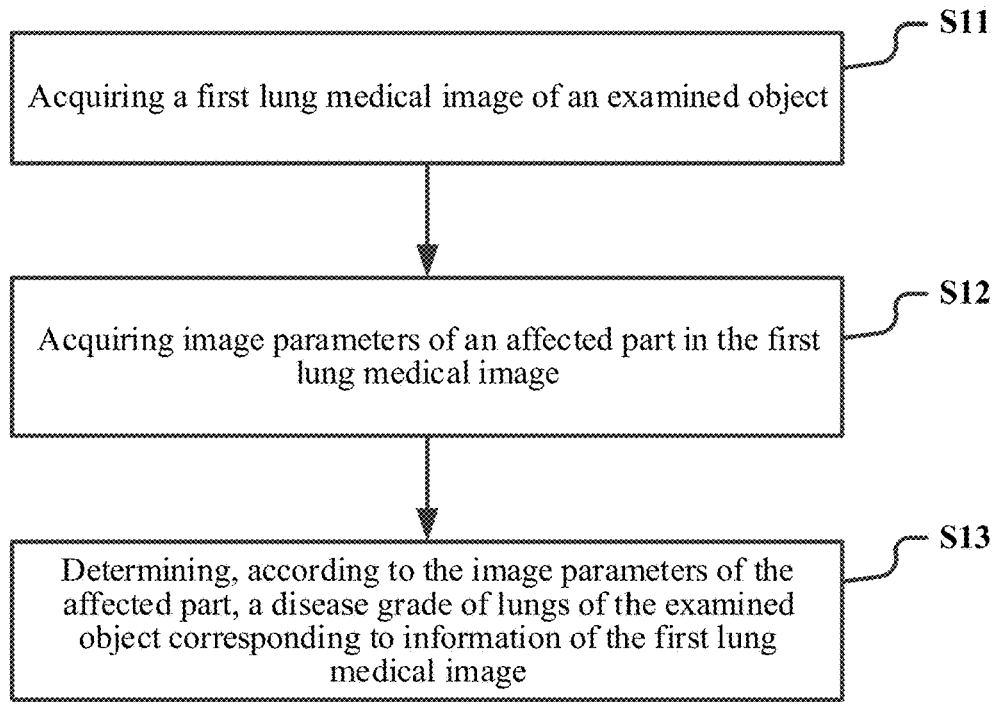
FIG. 1A is a flowchart of a diagnostic information processing method based on a medical image in an embodiment of the present invention.

FIG. 1A is a flowchart of a diagnostic information processing method based on a medical image in an embodiment of the present invention. As shown in FIG. 1A, the method may be implemented as the following steps S11-S13.

In step S11, a first lung medical image of an examined object is acquired.

In step S12, image parameters of an affected part in the first lung medical image are acquired.

In step S13, a disease grade of lungs of the examined object corresponding to information of the first lung medical image is determined according to the image parameters of the affected part.

Figure 1B:
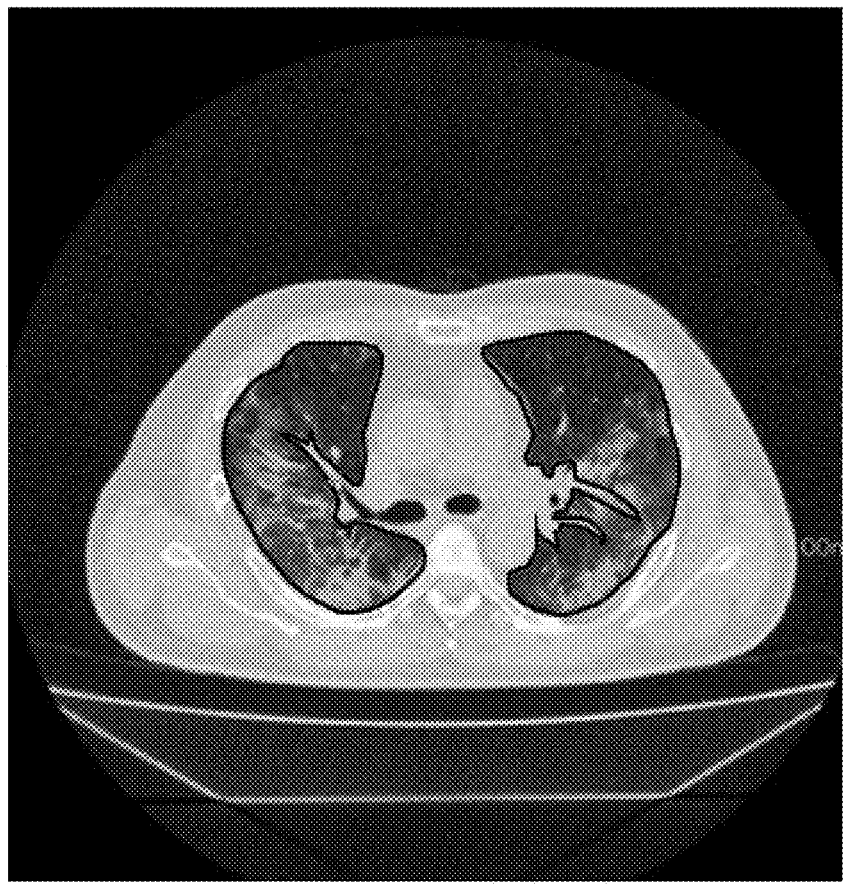
FIG. 1B is a schematic diagram of annotating a lung region in a medical image by a segmentation line.

In this embodiment, the first lung medical image of the examined object is acquired. The first lung medical image may be a CT image of the chest of the examined object. In this CT image, the lung region has been annotated. Specifically, this can be achieved by manual annotation. Certainly, before step S11, a step of segmenting a lung region may also be included. Specifically, a chest medical image is input into a pre-trained neuron network for segmenting the lung region, so that the lung region in the chest medical image can be identified and annotated through the neuron network. Specifically, after lungs are identified through the neuron network, the lungs are annotated by segmentation lines. As shown in FIG. 1B, the lungs are annotated by black segmentation lines. It can be understood that the segmentation lines may also be other colors. Through this segmentation step, the annotation of the lung region in the chest image can be realized, so as to obtain the first lung medical image. Certainly, this segmentation step can also allow a user to verify the accuracy of the segmentation result.

The CT value of the affected part in the medical image is different from the CT value of a normal lung region. In the medical field, involvement refers to the functional or organic changes of the tissue of an organ or a certain part caused by a disease, and the affected part refers to a part where functional or organic changes occur as a result of disease. The CT value of the affected part in the medical image is different from the CT value of a normal lung region. In the medical field, involvement refers to the functional or organic changes of the tissue of an organ or a certain part caused by a disease, and the affected part refers to a part where functional or organic changes occur as a result of disease. In clinical practice, a CT chest image can display and represent a corresponding lesion site through the image of the affected part, such as the lungs infected by coronaviruses, such as novel coronavirus, and 2019-nCoV virus. From the following detailed description, it should be considered that the present application can be specifically detailed to the processing of lesion information, the display of lesion images, and the output of corresponding diagnostic information on all lobes included in the lungs.

The image parameters of the affected part in the first lung medical image are acquired, specifically, at least one first lung medical image can be input into the neuron network to determine the image parameters of the affected part in the first lung medical image. Typically, the image parameters include a volume of the affected part.

The disease grade of the lungs of the examined object corresponding to the information of the first lung medical image is determined according to the image parameters of the affected part, specifically, the disease grade of the lungs of the examined object corresponding to the information of the first lung medical image can be determined in the following manners.

Manner 1

A relationship table is pre-created. The relationship table includes a corresponding relationship between the volume of the affected part and the disease grade. The volume of the affected part can be compared with a target relationship table, where the target relationship table stores the corresponding relationship between the volume of the affected part and the disease grade; and the disease grade of the lungs of the examined object can be determined according to the comparison result.

Manner 2

A volume proportion of the affected part in the lungs is calculated; and the volume of the affected part and the volume proportion of the affected part in the lungs are input into a disease grade calculation model, to obtain the disease grade of the lungs of the examined object that is comprehensively calculated by the disease grade calculation module based on the volume of the affected part and the volume proportion of the affected part in the lungs.

The present invention has the following beneficial effects: the image parameters of the affected part in the first lung medical image can be acquired, and then the disease grade of the lungs of the examined object corresponding to the information of the first lung medical image can be determined according to the image parameters of the affected part, so that a disease can be graded based on a medical image.

In one embodiment, step S12 may be implemented as the following step:

inputting at least one first lung medical image into a neuron network to determine a volume of the affected part in the first lung medical image.

In one embodiment, the neuron network includes:

a first detection model configured to detect a candidate patch shadow, a cutting model, a second detection model configured to detect a patch shadow interval, and a volume calculation model configured to calculate the volume of the affected part.

In the above-mentioned step, a normal CT value distribution interval in the lungs, a CT value distribution interval of the affected part, and at least one first lung medical image are input into the neuron network to determine the volume of the affected part in the first lung medical image. The step may be implemented as the following steps A1-A6.

In step A1, the at least one first lung medical image is passed through N consecutive convolution feature extraction modules in the first detection model, so that the N consecutive convolution feature extraction modules obtain image features of a patch shadow in the first lung medical image, where N is a positive integer.

In step A2, image features of the affected part in the first lung medical image are input into a fully connected layer in the first detection model, so that the fully connected layer outputs the candidate patch shadow based on the image features.

In step A3, the candidate patch shadow is passed through the cutting model, so that the cutting model cuts the candidate patch shadow in different directions in space multiple times to obtain multiple section images of the candidate patch shadow in multiple directions in space;

In step A4, multiple consecutive section images are passed through M consecutive convolution feature extraction modules in the second detection model, so that the M consecutive convolution feature extraction modules obtain image features of the section images, where M is a positive integer.

In step A5, the image features of the section images are input into a fully connected layer in the second detection model, so that the fully connected layer outputs patch shadow information based on the image features.

In step A6, the patch shadow information is passed through the volume calculation model, so that the volume calculation model calculates the volume of the affected part in the first lung medical image.

In this embodiment, the neuron network is formed by connecting a variety of models. The neuron network includes a first detection model configured to detect a candidate patch shadow, a cutting model, a second detection model configured to detect a patch shadow interval, and a volume calculation model configured to calculate the volume of the affected part.

The first detection model includes an input layer, N consecutive convolution feature extraction modules, a fully connected layer, and an output layer. The convolution feature extraction modules each include multiple convolution modules. The convolution modules each include a convolution layer, a BN layer, and an actuation layer.

The structure of the second detection model is the same as that of the first detection model, and is not repeated here.

When the at least one first lung medical image is passed through the N consecutive convolution feature extraction modules in the first detection model, for any three consecutive convolution feature extraction modules among the N convolution feature extraction modules, the image features output by the first convolution feature extraction module and the second convolution feature extraction module are added as the input of a third convolution feature extraction module. Similarly, when the multiple consecutive section images are passed through the M consecutive convolution feature extraction modules in the second detection model, for any three consecutive convolution feature extraction modules among the M convolution feature extraction modules, the image features output by the first convolution feature extraction module and the second convolution feature extraction module are added as the input of the third convolution feature extraction module.

In addition, in the above-mentioned step, the number M of the convolution feature extraction modules in the second detection model may be equal to the number N of the convolution feature extraction modules in the first detection model, and may also be not equal to N.

This embodiments has the following beneficial effects: the neuron network formed by connecting multiple models can simultaneously realize patch shadow detection and volume calculation, thereby simplifying the method for determining the volume of the affected part.

Figure 2A:
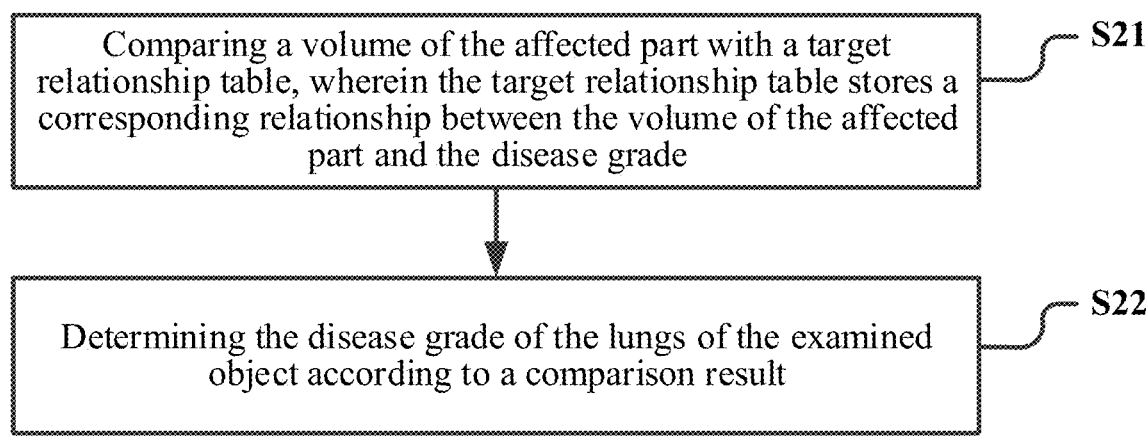
FIG. 2A is a flowchart of a diagnostic information processing method based on a medical image in another embodiment of the present invention.

In one embodiment, as shown in FIG. 2A, step S13 may be implemented as the following steps S21-S22.

In step S21, a volume of the affected part is compared with a target relationship table. The target relationship table stores a corresponding relationship between the volume of the affected part and the disease grade.

In step S22, the disease grade of the lungs of the examined object is determined according to a comparison result.

In this embodiment, a relationship table is pre-created. The relationship table includes a corresponding relationship between the volume of the affected part and the disease grade. The volume of the affected part can be compared with a target relationship table, where the target relationship table stores the corresponding relationship between the volume of the affected part and the disease grade; and the disease grade of the lungs of the examined object can be determined according to the comparison result.

In one embodiment, step S13 may be implemented as the following steps B1-B2.

In step B1, a volume proportion of the affected part in the lungs is calculated.

In step B2, the volume of the affected part and the volume proportion of the affected part in the lungs are input into a disease grade calculation model, to obtain the disease grade of the lungs of the examined object that is comprehensively calculated by the disease grade calculation module based on the volume of the affected part and the volume proportion of the affected part in the lungs.

In this embodiment, the volume proportion of the affected part in the lungs is calculated; and the volume of the affected part and the volume proportion of the affected part in the lungs are input into a disease grade calculation model, to obtain the disease grade of the lungs of the examined object that is comprehensively calculated by the disease grade calculation module based on the volume of the affected part and the volume proportion of the affected part in the lungs.

Figure 2B:
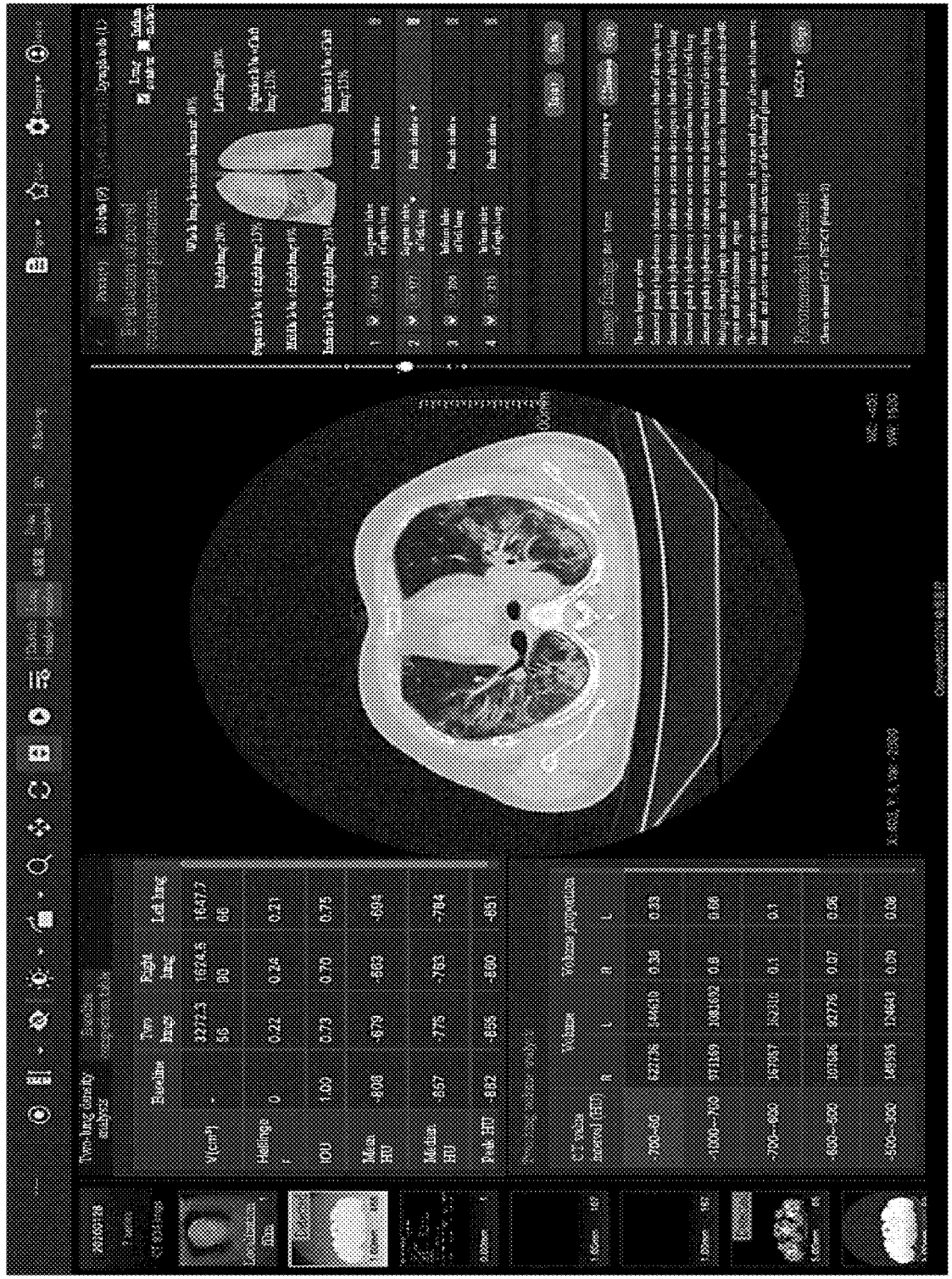
FIG. 2B is a schematic diagram of an interface of a system implementing the solution provided by the present invention.

In this embodiment, the volume proportion of a specific affected part in the lungs can also be calculated by a pre-trained volume proportion calculation model. After the medical image is input into the volume proportion calculation model, the model can automatically give the volume proportion of each CT interval. FIG. 2B is a schematic diagram of an interface of a system implementing the solution provided by the present invention. As shown in FIG. 2B, the volume of an affected region calculated by the volume proportion calculation model is displayed in a two-lung volume analysis column of the schematic diagram of the interface.

Figure 3A:
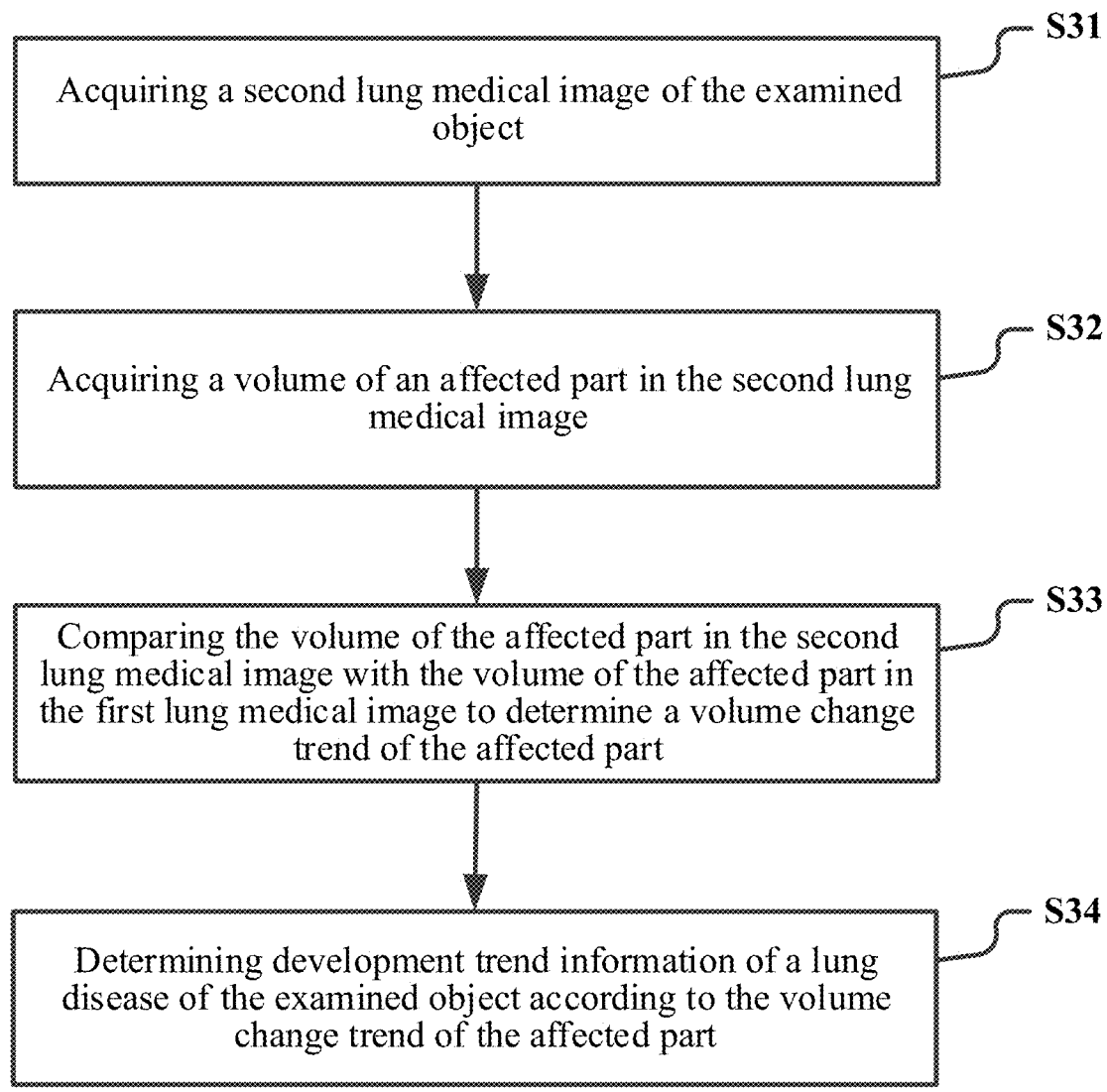
FIG. 3A is a flowchart of a diagnostic information processing method based on a medical image in yet another embodiment of the present invention.

In one embodiment, as shown in FIG. 3A, the method can further be implemented as the following steps S31-S34.

In step S31, a second lung medical image of an examined object is acquired.

In step S32, a volume of an affected part in the second lung medical image is acquired.

In step S33, the volume of the affected part in the second lung medical image is compared with the volume of the affected part in the first lung medical image to determine a volume change trend of the affected part.

In step S34, development trend information of a lung disease of the examined object is determined according to the volume change trend of the affected part.

In this embodiment, the second lung medical image of an examined object is acquired. The second lung medical image and the first lung medical image in the foregoing embodiments are lung medical images of the same examined object in different periods. The volume of the affected part in the second lung medical image is compared with the volume of the affected part in the first lung medical image to determine the volume change trend of the affected part. The development trend information of the lung disease of the examined object is determined according to the volume change trend of the affected part.

Figure 3B:
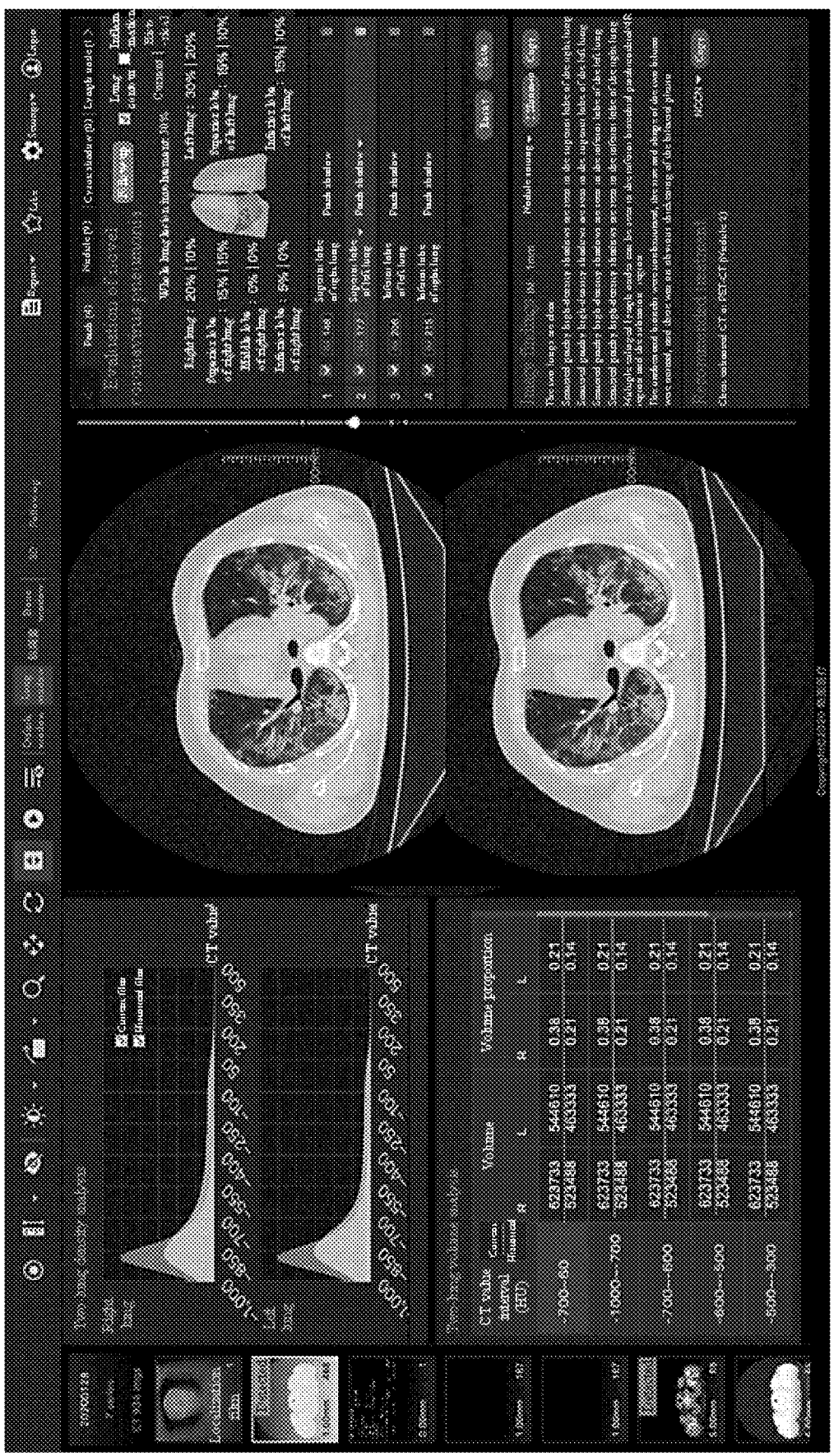
FIG. 3B is a schematic diagram of development trend evaluation of novel coronavirus pneumonia in different disease courses.

For example, the condition of the examined object may be exacerbated and relieved over time. Therefore, the development trend information of the lung disease of the examined object can be determined based on the lung medical images in different time periods. Specifically, an ID of the examined object is acquired, and the second lung medical image of the examined object is obtained based on the ID of the examined object. The generation time of the second lung medical image may be earlier than the first lung medical image, or may be later than the first lung medical image, as long as the generation time of the first lung medical image is different from that of the second lung medical image. In addition, considering that the change of the disease condition is not obvious if the time span is too small, the interval between the generation time of the first lung medical image and the generation time of the second lung medical image is not less than a certain value, such as 48 hours. FIG. 3B is a schematic diagram of evaluation of novel coronavirus pneumonia. The schematic diagram includes the comparison result of the first lung medical image and the second lung medical image. As shown in FIG. 3B, after the second lung medical image of the examined object is acquired, the volume of the affected part in the second lung medical image is acquired, and then the volume of the affected part in the second lung medical image compared with the volume of the affected part in the first lung medical image to determine the volume change trend of the affected part. The development trend information of the lung disease of the examined object is determined according to the volume change trend of the affected part. For example, in FIG. 3B, as can be seen from the novel pneumonia evaluation interface on the right side of the figure, the volume of the affected part of the right lung decreases from 20% to 10%, and the volume of the affected part of the left lung decreases from 30% to 20%, i.e., the volume of the affected part decreases over time, and it is determined that the condition of the lung disease of the examined object is relieved. It can be understood that, if the volume of the affected part increases over time, it is determined that the condition of the lung disease of the examined object is exacerbated. Furthermore, the volume change trend of the affected part can be indicated in a more intuitive manner, for example, the volume change trend of the affected part is indicated using arrows, and the volume change trend of the affected part is indicated using arrows in combination with specific values. Certainly, the volume change trend can also be indicated in other manners, which are not detailed here.

This embodiments has the following beneficial effects: the volume change trend of the affected part can be determined based on different lung medical images of the same examined object, so that the development trend information of the lung disease of the examined object is automatically determined through the volume change trend of the affected part.

In one embodiment, step S34 may be implemented as the following steps C1-C2.

In step C1, when the volume of the affected part conforms to a first trend, a first diagnostic result of the examined object is determined.

In step C2, when the volume of the affected part conforms to a second trend, a second diagnostic result of the examined object is determined.

When the volume of the affected part conforms to the first trend, determining the first diagnostic result of the examined object is determined.

For example, assuming that the generation time of the first lung medical image is later than that of the second lung medical image, when the volume of the affected part in the first lung medical image is less than the volume of the affected part in the second lung medical image, the volume of the affected part decreases. Assuming that the generation time of the first lung medical image is earlier than that of the second lung medical image, when the volume of the affected part in the first lung medical image is greater than the volume of the affected part in the second lung medical image, the volume of the affected part decreases. When the volume of the affected part decreases, the first diagnostic result of the examined object is determined, that is, the condition of the examined object is being relieved.

When the volume of the affected part conforms to the second trend, the second diagnostic result of the examined object is determined.

Assuming that the generation time of the first lung medical image is later than that of the second lung medical image, when the volume of the affected part in the first lung medical image is greater than the volume of the affected part in the second lung medical image, the volume of the affected part increases. Assuming that the generation time of the first lung medical image is earlier than that of the second lung medical image, when the volume of the affected part in the first lung medical image is less than the volume of the affected part in the second lung medical image, the volume of the affected part increases. When the volume of the affected part increases, the second diagnostic result of the examined object is determined, that is, the condition of the examined object is being exacerbated.

In one embodiment, the method can further be implemented as the following steps D1-D2.

In step D1, generation time of the first lung medical image and the second lung medical image is acquired.

In step D2, a disease development speed of the examined object is calculated according to the generation time and the volume change trend of the affected part.

In this embodiment, the generation time of the first lung medical image and the second lung medical image can be acquired. According to the generation time, an interval between the generation time of the first lung medical image and the generation time the second lung medical image is determined, and then a volume change range of the affected part per unit time is calculated based on the time interval and a volume change range of the affected part, so as to obtain the disease development speed of the examined object.

In one embodiment, the method can further be implemented as the following steps E1 and/or E2-E3.

In step E1, the first lung medical image is rendered based on a single color to generate a third lung medical image, where a color depth after rendering is positively correlated with a CT value.

In step E2, the first lung medical image is rendered based on multiple colors to generate a fourth lung medical image, where different CT values are rendered with different types of colors.

In step E3, the first lung medical image, the third lung medical image and/or the fourth lung medical image is output.

Figure 3C:
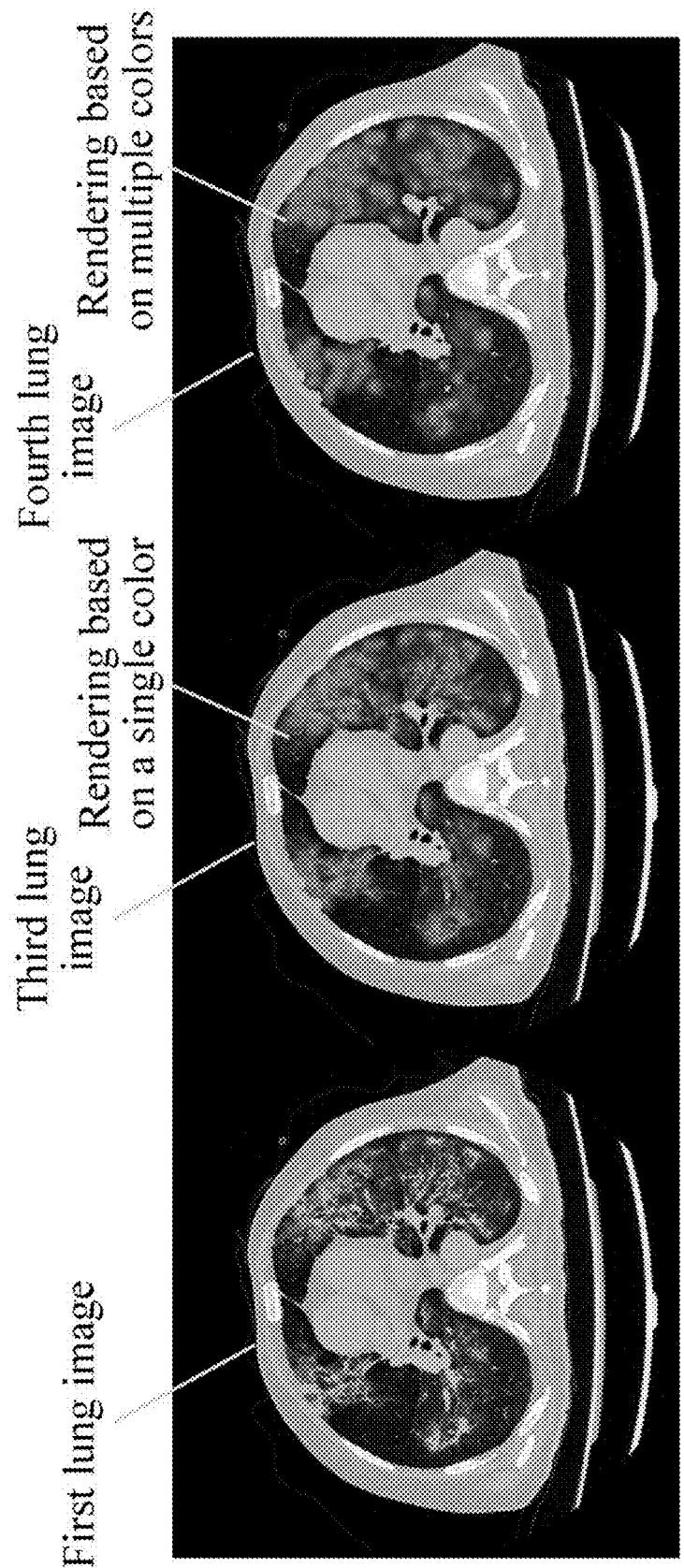
FIG. 3C is a comparison diagram of a first lung medical image and lung medical images rendered in different manners.

In this embodiment, in order to verify the accuracy of CT value interval segmentation, the volume of a lesion can be displayed according to the CT value interval selected by a user and displayed in the form of "rendering". Specifically, the first lung medical image is rendered based on a single color to generate the third lung medical image, where the color depth after the rendering is positively correlated with the CT value; next, the first lung medical image is rendered based on multiple colors to generate the fourth lung medical image, where different CT values are rendered with different types of colors; and then the first lung medical image, the third lung medical image and the fourth lung medical image are output. The specific output image format may be shown in FIG. 3C, and the left side is the first lung medical image of the examined object. In this example, the first lung medical image is a chest CT image including the lungs. In the cross-sectional view in the middle, the first lung medical image is rendered with one color, and different CT values adopt different depths, for example, the higher the CT value is, the darker the color is. Certainly, it can be understood that the following setting is also acceptable: the higher the CT value is, the lighter the color is. In the cross-sectional view on the right, changing colors are used for marking. For example, multiple CT value intervals can be set. Regions falling within an interval of low CT values are rendered in blue, and regions falling within an interval of high CT values are rendered in red.

It can be understood that, in step E3, it is possible to output only the first lung medical image and the third lung medical image, to output only the first lung medical image and the fourth lung medical image, or to simultaneously output the first lung medical image, the third lung medical image and the fourth lung medical image.

In one embodiment, the method can further be implemented as the following steps F1-F2.

In step F1, multiple lung medical images are rendered with multiple colors, where portions of the rendered lung medical images having different CT values and/or CT value ranges correspond to different colors.

In step F2, multiple rendered lung medical images are output.

In this embodiment, it is possible to render lung medical images of the same patient in different disease courses to enhance the comparison effect. For example, the lung medical images of the same examined object for three consecutive days are rendered with multiple colors. Portions of the rendered lung medical images having different CT values and/or CT value ranges correspond to different colors. Then, the multiple rendered lung medical images are output. Thus, CT images mainly in black and white are rendered into color images, which enhances the effect of the images and obtains the rendered lung medical images of the same examined object in different disease courses, thereby facilitating comparison of disease conditions of different disease courses.

Figure 3D:
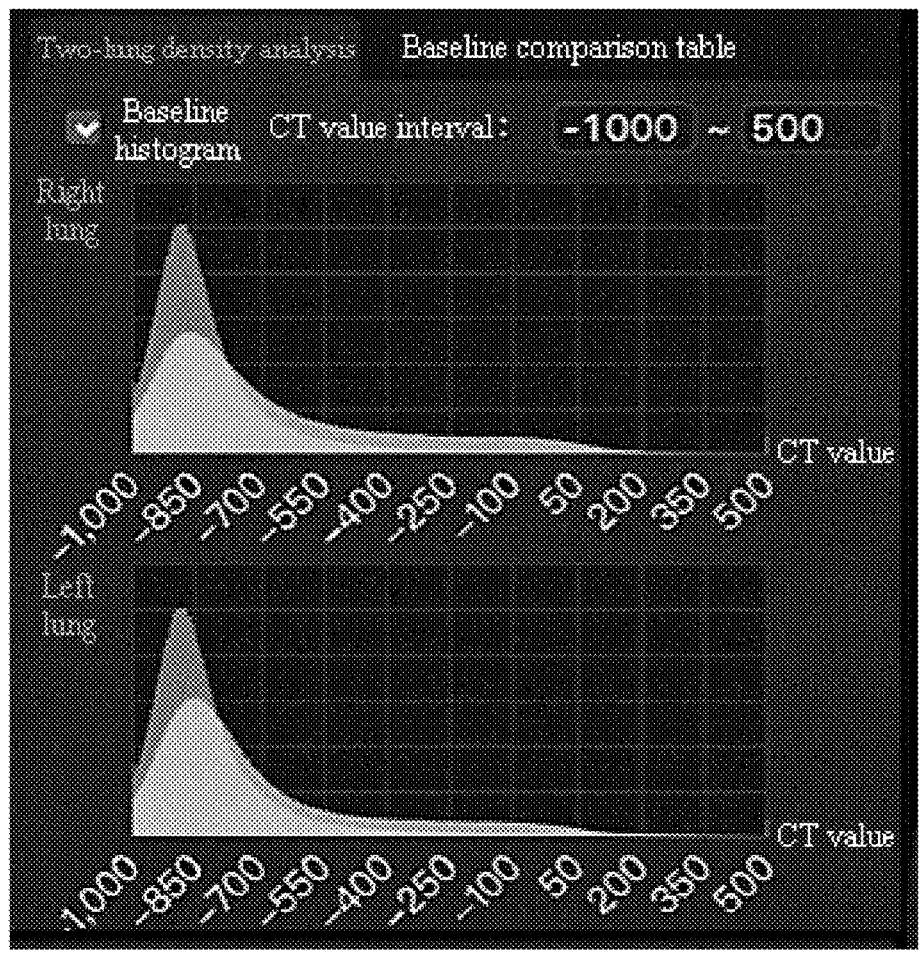
FIG. 3D is a comparative schematic diagram showing the distribution of CT values of normal lungs and CT values of lungs with specific diseases.

In addition, it should be noted that, for different diseases, a comparative schematic diagram showing the distribution of CT values of normal lungs and CT values of lungs with specific diseases can be given. For example, for novel coronavirus pneumonia, by analyzing a large number of chest CT images of healthy people, CT value data in the lungs of normal people can be given as a baseline reference, and histograms are drawn, to provide the joint intersection, Hellinger coefficient, etc. of the CT value distribution of the healthy people and patients, for doctors to compare. The specific comparative schematic diagram is shown in FIG. 3D. The CT histogram with a large change range is a histogram corresponding to the novel coronavirus pneumonia, and according to this histogram, the current severity of the novel coronavirus pneumonia can be accurately and quickly evaluated.

Figure 4:
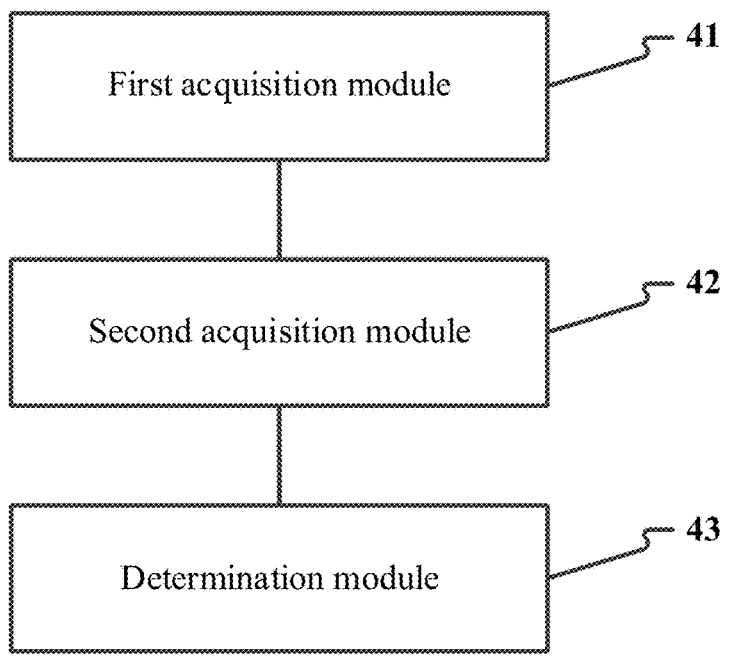
FIG. 4 is a block diagram of a diagnostic information processing apparatus based on a medical image in an embodiment of the present invention.

FIG. 4 is a block diagram of a diagnostic information processing apparatus or display apparatus or interaction apparatus based on a medical image in an embodiment of the present invention. As shown in FIG. 4, the apparatus includes:

a first acquisition module 41, configured to acquire a first lung medical image of an examined object;

a second acquisition module 42, configured to acquire image parameters of an affected part in the first lung medical image; and a determination module 43, configured to determine, according to the image parameters of the affected part, a disease grade of lungs of the examined object corresponding to information of the first lung medical image.

In one embodiment, the second acquisition module includes:

an input submodule, configured to input at least one first lung medical image into a neuron network to determine a volume of the affected part in the first lung medical image.

In one embodiment, the neuron network includes:

a first detection model configured to detect a candidate patch shadow, a cutting model, a second detection model configured to detect a patch shadow interval, and a volume calculation model configured to calculate the volume of the affected part; and the input submodule is configured to:
  pass the at least one first lung medical image through N consecutive convolution feature extraction modules in the first detection model, so that the N consecutive convolution feature extraction modules obtain image features of a patch shadow in the first lung medical image, where N is a positive integer;
  input image features of the affected part in the first lung medical image into a fully connected layer in the first detection model, so that the fully connected layer outputs the candidate patch shadow based on the image features;
  pass the candidate patch shadow through the cutting model, so that the cutting model cuts the candidate patch shadow in different directions in space multiple times to obtain multiple section images of the candidate patch shadow in multiple directions in space;
  pass multiple consecutive section images through M consecutive convolution feature extraction modules in the second detection model, so that the M consecutive convolution feature extraction modules obtain image features of the section images, where M is a positive integer;

input the image features of the section images into a fully connected layer in the second detection model, so that the fully connected layer outputs patch shadow information based on the image features; and pass the patch shadow information through the volume calculation model, so that the volume calculation model calculates the volume of the affected part in the first lung medical image.

In one embodiment, the determination module includes:

a comparison submodule, configured to compare a volume of the affected part with a target relationship table, where the target relationship table stores a corresponding relationship between the volume of the affected part and the disease grade; and a first determination submodule, configured to determine the disease grade of the lungs of the examined object according to a comparison result.

In one embodiment, the determination module includes:

a calculation submodule, configured to calculate a volume proportion of the affected part in the lungs; and an input submodule, configured to input a volume of the affected part and the volume proportion of the affected part in the lungs into a disease grade calculation model, to obtain the disease grade of the lungs of the examined object that is comprehensively calculated by the disease grade calculation module based on the volume of the affected part and the volume proportion of the affected part in the lungs.

In one embodiment, the apparatus further includes:

a third acquisition module, configured to acquire a second lung medical image of the examined object;

a fourth acquisition module, configured to acquire a volume of an affected part in the second lung medical image;

a comparison module, configured to compare the volume of the affected part in the second lung medical image with the volume of the affected part in the first lung medical image to determine a volume change trend of the affected part; and a change trend determination module, configured to determine development trend information of a lung disease of the examined object according to the volume change trend of the affected part.

In one embodiment, the change trend determination module includes:

a second determination submodule, configured to determine, when the volume of the affected part conforms to a first trend, a first diagnostic result of the examined object; and a third determination submodule, configured to determine, when the volume of the affected part conforms to a second trend, a second diagnostic result of the examined object.

In one embodiment, the apparatus further includes:

a fifth acquisition module, configured to acquire generation time of the first lung medical image and the second lung medical image; and a calculation module, configured to calculate a disease development speed of the examined object according to the generation time and the volume change trend of the affected part.

In one embodiment, the apparatus further includes:

a first rendering module, configured to render the first lung medical image based on a single color to generate a third lung medical image, where a color depth after rendering is positively correlated with a CT value;

a second rendering module, configured to render the first lung medical image based on multiple colors to generate a fourth lung medical image, where different CT values are rendered with different types of colors; and a first output module, configured to output the first lung medical image, the third lung medical image and/or the fourth lung medical image.

In one embodiment, the apparatus further includes:

a third rendering module, configured to render multiple lung medical images with multiple colors, where portions of the rendered lung medical images having different CT values and/or CT value ranges correspond to different colors; and a second output module, configured to output multiple rendered lung medical images.

Figure 5:
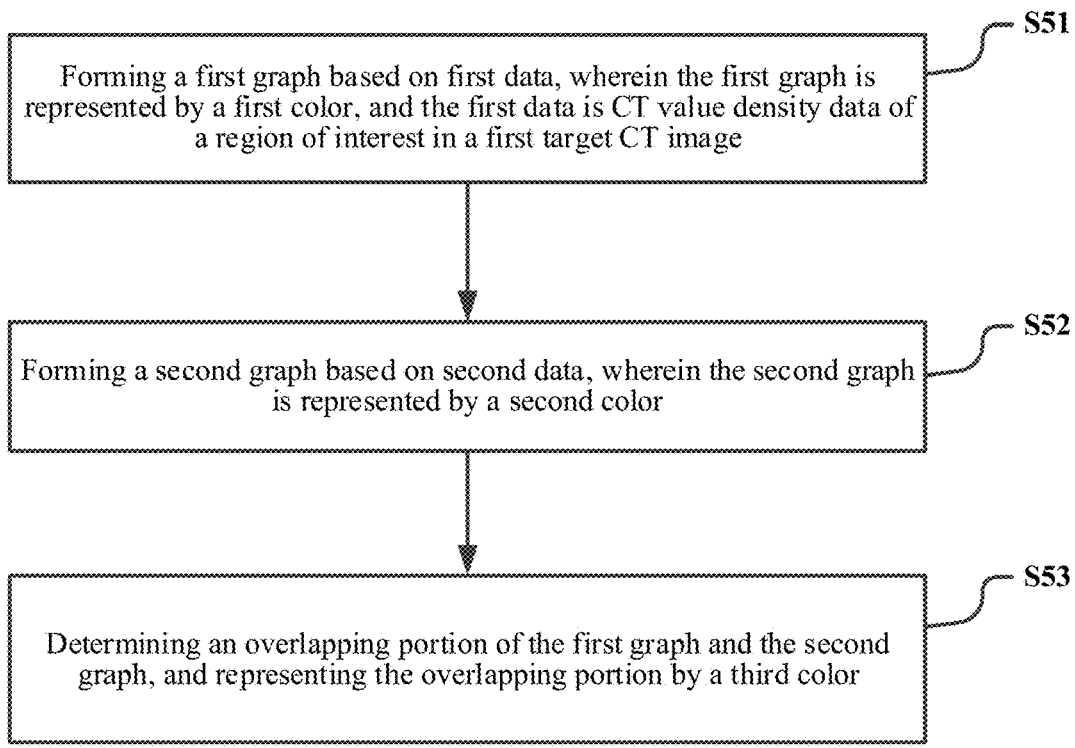
FIG. 5 is a flowchart of a method for displaying a diagnostic information interface in an embodiment of the present invention.

FIG. 5 is a flowchart of a method for displaying a diagnostic information interface in an embodiment of the present invention. As shown in FIG. 5, the method may be implemented as the following steps S51-S53.

In step S51, a first graph is formed based on first data, where the first graph is represented by a first color, and the first data is CT value density data of a region of interest in a first target CT image.

In step S52, a second graph is formed based on second data, where the second graph is represented by a second color.

In step S53, an overlapping portion of the first graph and the second graph is determined, and the overlapping portion is represented by a third color.

In this embodiment, the first graph is formed based on the first data. Specifically, the first data can be obtained by: determining the first data in response to acquiring the CT value density data of the region of interest in the first target CT image. Then, the second graph is formed based on second data.

Figure 6:
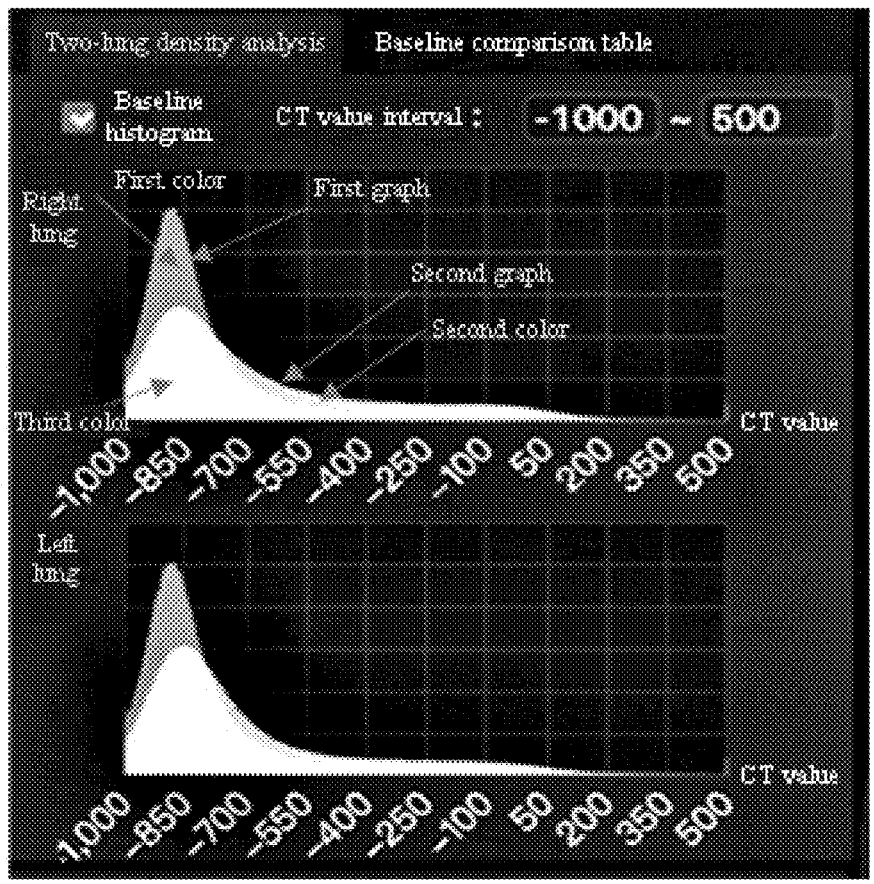
FIG. 6 is a comparative schematic diagram including a first graph and a second graph.

When the first graph and the second graph are histograms corresponding to the CT value density data, as shown in FIG. 3D or FIG. 6, after the first graph and the second graph are formed, the first graph and the second graph can be put in the same coordinate system, so as to form a comparison diagram of probability distribution of CT values of the first target CT image and other data, so that the severity of the disease in the first target CT image can be more intuitively represented by the first graph and the second graph. The histograms in the various embodiments involved in the present disclosure may be constructed based on 3D medical images, for example, based on particles of the corresponding part in a 3D CT chest image. Therefore, the histograms involved in the present disclosure may be defined as 3D-CT value histograms.

The present application has the following beneficial effects: the first graph is formed based on the first data, and the second graph is formed based on the second data, where the first data is CT value density data of a region of interest in the first target CT image, so that the first data can be compared with the second data; when the second data is the normal CT value density data of the corresponding part of the CT image, it is convenient for the user to determine the severity of the disease based on the comparison between the first graph and the second graph. Therefore, such a solution can make the representation form of the severity of the disease more intuitive.

In one embodiment, the forming a first graph based on first data includes:

determining the first data in response to acquiring the CT value density data of the region of interest in the first target CT image.

In one embodiment, the second data is benchmark data of a region of interest in a CT image.

In this embodiment, the second data is the benchmark data of the region of interest in the CT image. The benchmark data may be data defined by a doctor as the benchmark data, standard data in industry, or average data of normal people. For example, assuming that the first data is CT value density data of lungs of a patient with a lung disease (such as a patient with novel coronavirus pneumonia), the second data may be user-defined data, standard data in industry, average data of normal people, or the CT value density data of the lungs of the patient with the lung disease in other time periods (e.g., before suffering from the disease or after recovery).

Assuming that the second data is the average data of normal people, the lower the similarity between the first graph and the second graph is, the higher the severity of the disease of the examined object corresponding to the first target CT image is, and the higher the similarity is, the lower the severity of the disease of the examined object is. Moreover, when the similarity between the first graph and the second graph is greater than a certain value (such as, 95%), it can be considered that the examined object is not sick or has recovered.

In one embodiment, the second data is CT value density data of a region of interest in a second target CT image obtained at different time from the first target CT image.

In this embodiment, the second data is the CT value density data of the region of interest in the second target CT image obtained at different time from the first target CT image. For example, for the same examined object, the CT value density data of the examined object in different periods is obtained, so that the development trend of the lung disease of the examined object can be more intuitively represented.

In one embodiment, the region of interest includes at least one of the following regions: human lung organ, left lung, right lung, superior lobe of right lung, middle lobe of right lung, inferior lobe of right lung, superior lobe of left lung, or inferior lobe of left lung.

In the field of machine vision and image processing, a region to be processed is outlined from the processed image in the form of blocks, circles, ellipses, irregular polygons, etc., and is called the region of interest. In this embodiment, the region of interest may include at least one of the following regions:

human lung organ, left lung, right lung, superior lobe of right lung, middle lobe of right lung, inferior lobe of right lung, superior lobe of left lung, or inferior lobe of left lung.

For example, the human lung organ can be outlined by a shape that fits perfectly with the human lung organ. For example, in FIG. 1B, the human lung organ outlined by the black irregular polygon is the region of interest, so that subsequent algorithms can focus on the region of interest, thereby reducing the amount of calculation in subsequent processing steps.

Figure 7:
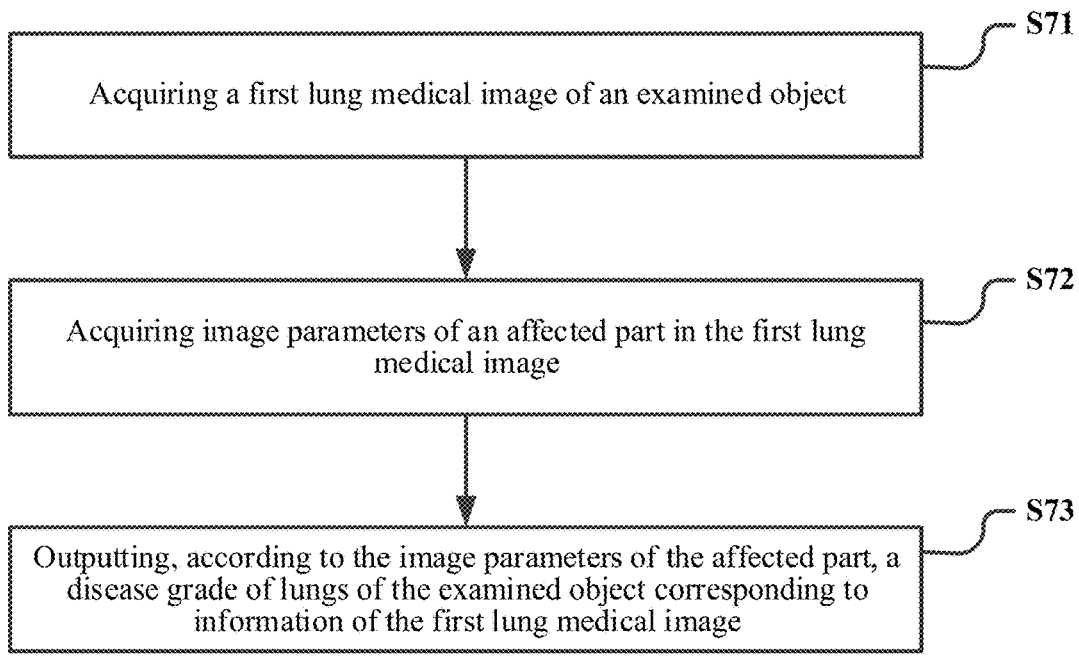
FIG. 7 is a flowchart of a diagnostic information interaction method based on a medical image in an embodiment of the present invention.

FIG. 7 is a flowchart of a diagnostic information interaction method based on a medical image in an embodiment of the present invention. As shown in FIG. 7, the method may be implemented as the following steps S71-S73.

In step S71, a first lung medical image of an examined object is acquired.

In step S72, image parameters of an affected part in the first lung medical image are acquired.

In step S73, a disease grade of lungs of the examined object corresponding to information of the first lung medical image is output according to the image parameters of the affected part.

It should be understood that the interaction method of the embodiments involved in the present disclosure may be based on the necessary diagnostic information processing method, and includes determining the disease grade of the lungs of the examined object corresponding to the corresponding information of the first lung medical image.

It should be noted here that the first lung medical image involved in this embodiment may be the first target CT image involved in the foregoing embodiments.

Figure 8:
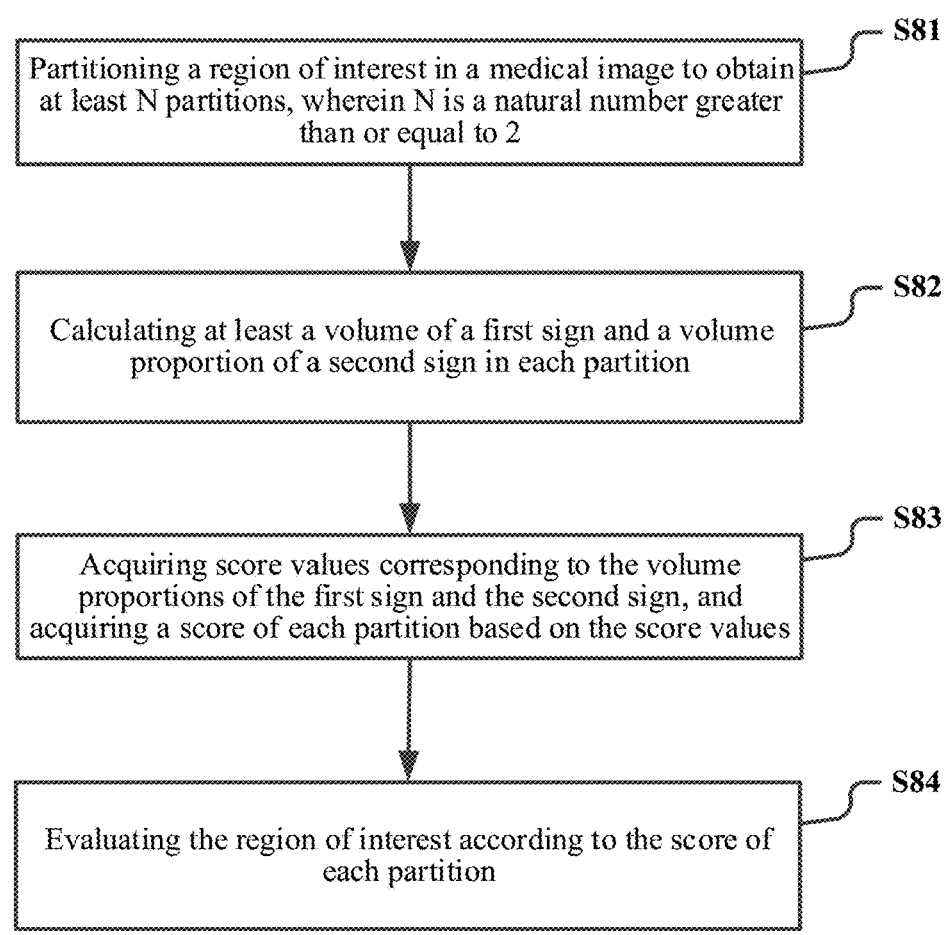
FIG. 8 is a flowchart of a diagnostic information evaluation method based on a medical image in an embodiment of the present invention.

FIG. 8 is a flowchart of a diagnostic information evaluation method based on a medical image in an embodiment of the present invention. As shown in FIG. 8, the method may be implemented as the following steps S81-S84.

In step S81, a region of interest in a medical image is partitioned to obtain at least N partitions, where N is a natural number greater than or equal to 2.

In step S82, at least a volume of a first sign and a volume proportion of a second sign in each partition are calculated.

In step S83, score values corresponding to the volume proportions of the first sign and the second sign are acquired, and a score of each partition is acquired based on the score values.

In step S84, the region of interest is evaluated according to the score of each partition.

In this embodiment, the region of interest in the medical image is partitioned to obtain at least N partitions, where N is a natural number greater than or equal to 2.

In the field of machine vision and image processing, a region to be processed is outlined from the processed image in the form of blocks, circles, ellipses, irregular polygons, etc., and is called the region of interest. In this embodiment, the region of interest in the medical image may be a certain human organ in the medical image. For example, when the medical image is a chest CT image, the region of interest may be a human lung organ, and the outlined region of interest is shown in FIG. 1B. The region of interest in the medical image can be partitioned in the following two manners.

Manner 1

At least N partitions of the region of interest are obtained. The region of interest is human lungs, and the N partitions are superior lobe of right lung, middle lobe of right lung, inferior lobe of right lung, superior lobe of left lung, and inferior lobe of left lung.

Manner 2

At least N partitions of the region of interest are obtained. The region of interest is human lungs, and the N partitions are six partitions obtained by partitioning each of left and right lungs of the human lungs into three parts from top to bottom.

After the N partitions are obtained, at least the volume of the first sign and the volume proportion of the second sign in each partition are calculated.

Specifically, when a disease to be detected is pneumonia, the pneumonia appears as a patch and/or ground glass in the CT image, that is, a patch shadow and a ground glass shadow can coexist in a lung CT image. Therefore, the first sign may refer to a patch region of a human lung CT image, and the second sign may refer to a ground glass region of the human lung CT image. It can be understood that different diseases have different signs. Therefore, for different diseases, signs to be calculated are different. By applying the solution disclosed in the present application, in addition to the volume proportion of the first sign and the volume proportion of the second sign, when the signs reflecting the diseases include other signs, the volume proportions of other signs can also be calculated. For example, various types of nodules, cavities, tree-in-bud signs, orbital signs, etc. have been used in clinical diagnostic practice to reflect disease signs.

The score values corresponding to the volume proportions of the first sign and the second sign are acquired, and the score of each partition is acquired based on the score values.

The region of interest is evaluated according to the score of each partition. Specifically, a corresponding score threshold can be set, and then the severity of the disease of the examined object corresponding to the medical image can be determined based on the score threshold.

The present application has the following beneficial effects: the region of interest in the medical image can be partitioned, and the score of each partition can be calculated, so as to realize the quantitative processing of the disease severity corresponding to the region of interest. Thus, the disease severity of the region of interest can be evaluated based on the scores obtained by the quantitative processing, thereby achieving the effect of evaluating the disease severity based on the disease region of the medical image.

In one embodiment, step S81 may be implemented as the following step:

obtaining at least N partitions of the region of interest, where the region of interest is human lungs, and the N partitions are superior lobe of right lung, middle lobe of right lung, inferior lobe of right lung, superior lobe of left lung, and inferior lobe of left lung.

The human lungs can be divided into five regions through structural division, which are superior lobe of right lung, middle lobe of right lung, inferior lobe of right lung, superior lobe of left lung, and inferior lobe of left lung, respectively. In this embodiment, the partitioning may be performed based on the division of human body distribution structure, that is, the N partitions are superior lobe of right lung, middle lobe of right lung, inferior lobe of right lung, superior lobe of left lung, and inferior lobe of left lung, respectively.

Figure 9:
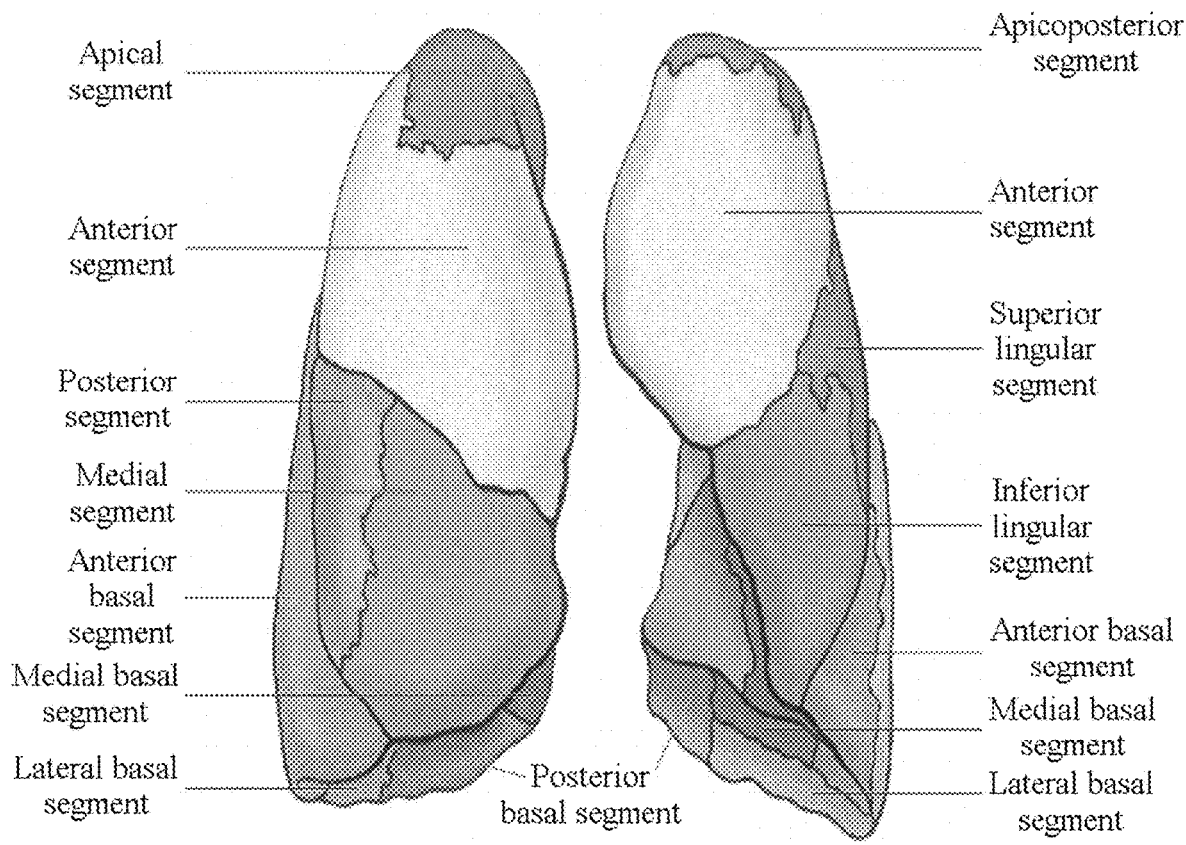
FIG. 9 is a schematic diagram showing the distribution of human lung segments in a medical image.

In addition, it can be understood that the N partitions can also be determined based on lung segments. FIG. 9 is a schematic diagram showing the distribution of human lung segments in a medical image. As shown in FIG. 9, the superior lobe of right lung includes: an apical segment, a posterior segment, and an anterior segment; the middle lobe of right lung includes a lateral segment and a medial segment; the inferior lobe of right lung includes a medial basal segment, an anterior basal segment, and a lateral basal segment; the superior lobe of left lung includes an apicoposterior segment, an anterior segment, a superior lingular segment, and inferior lingular segment; the inferior lobe of left lung includes an anterior basal segment, a lateral basal segment, and a medial basal segment. Thus, when the partitioning is based on the lung segments, each lung segment can be used as a partition.

Certainly, it can be understood that this partitioning manner is based on the lung segments that can be displayed in a lung medical image. Some regions that are not displayed are not annotated in FIG. 9, e.g., lung segment regions that are not displayed, such as a dorsal segment.

In one embodiment, step S81 can further be implemented as the following step:

obtaining at least N partitions of the region of interest, where the region of interest is human lungs, and the N partitions are six partitions obtained by partitioning each of left and right lungs of the human lungs into three parts from top to bottom.

Figure 10:
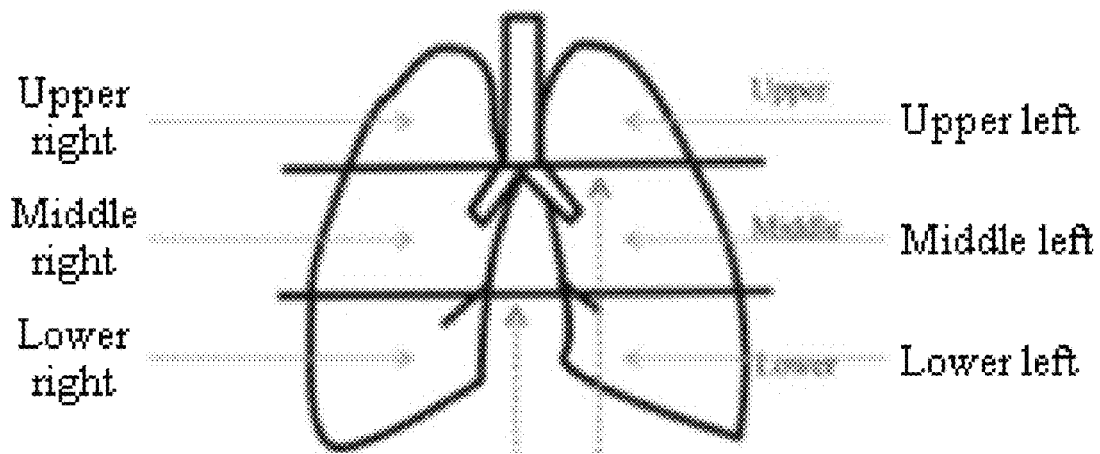
FIG. 10 is a schematic diagram of segmenting human lungs into six partitions by segmentation lines.

In this embodiment, the left lung and the right lung are each divided into three parts, thereby forming six partitions. Specifically, as shown in FIG. 10, the lung image is partitioned by two cutting lines, so that the lung image is divided into an upper right partition, a middle right partition, a lower right partition, an upper left partition, a middle left partition, and a lower left partition in total.

In one embodiment, the first sign is a patch region, and the second sign is a ground glass region.

When a disease to be detected is pneumonia, the pneumonia appears as a patch and/or ground glass in the CT image, that is, a patch shadow and a ground glass shadow can coexist in a lung CT image. Therefore, in this embodiment, the first sign may refer to a patch region of a human lung CT image, and the second sign may refer to a ground glass region of the human lung CT image.

Figure 11:
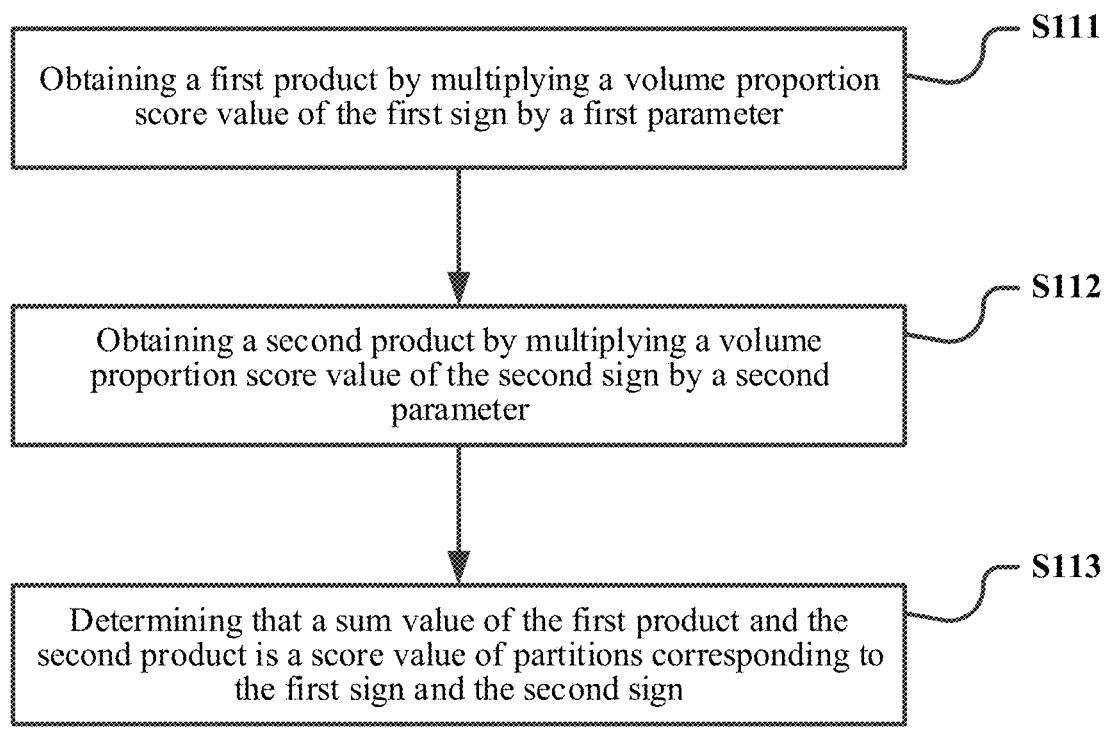
FIG. 11 is a flowchart of a diagnostic information evaluation method based on a medical image in an embodiment of the present invention.

In one embodiment, as shown in FIG. 11, step S83 can further be implemented as the following steps S111-S113.

In step S111, a first product is obtained by multiplying a volume proportion score value of the first sign by a first parameter.

In step S112, a second product is obtained by multiplying a volume proportion score value of the second sign by a second parameter.

In step S113, it is determined that a sum value of the first product and the second product is a score value of partitions corresponding to the first sign and the second sign.

In this embodiment, when obtaining the score of each partition, the first product is obtained by multiplying the volume proportion score value of the first sign by the first parameter, and the second product is obtained by multiplying the volume proportion score value of the second sign by the second parameter. The volume proportion score value of the first sign may be a score value obtained by multiplying the volume proportion of the first sign by a specific coefficient. It can be understood that, when the specific coefficient is 1, the volume proportion score value of the first sign is the volume proportion of the first sign itself. Similarly, the volume proportion score value of the second sign may be a score value obtained by multiplying the volume proportion of the second sign by the specific coefficient. In addition, the first parameter can be determined based on a relationship between the first sign and a probability of having a target disease, and the second parameter can be determined based on a relationship between the second sign and the probability of having the target disease.

For example, assuming that the first parameter is 3 and the second parameter is 2, then the score of a partition may be the first sign volume proportion score value×3+the second sign volume proportion score value×2.

Figure 12:
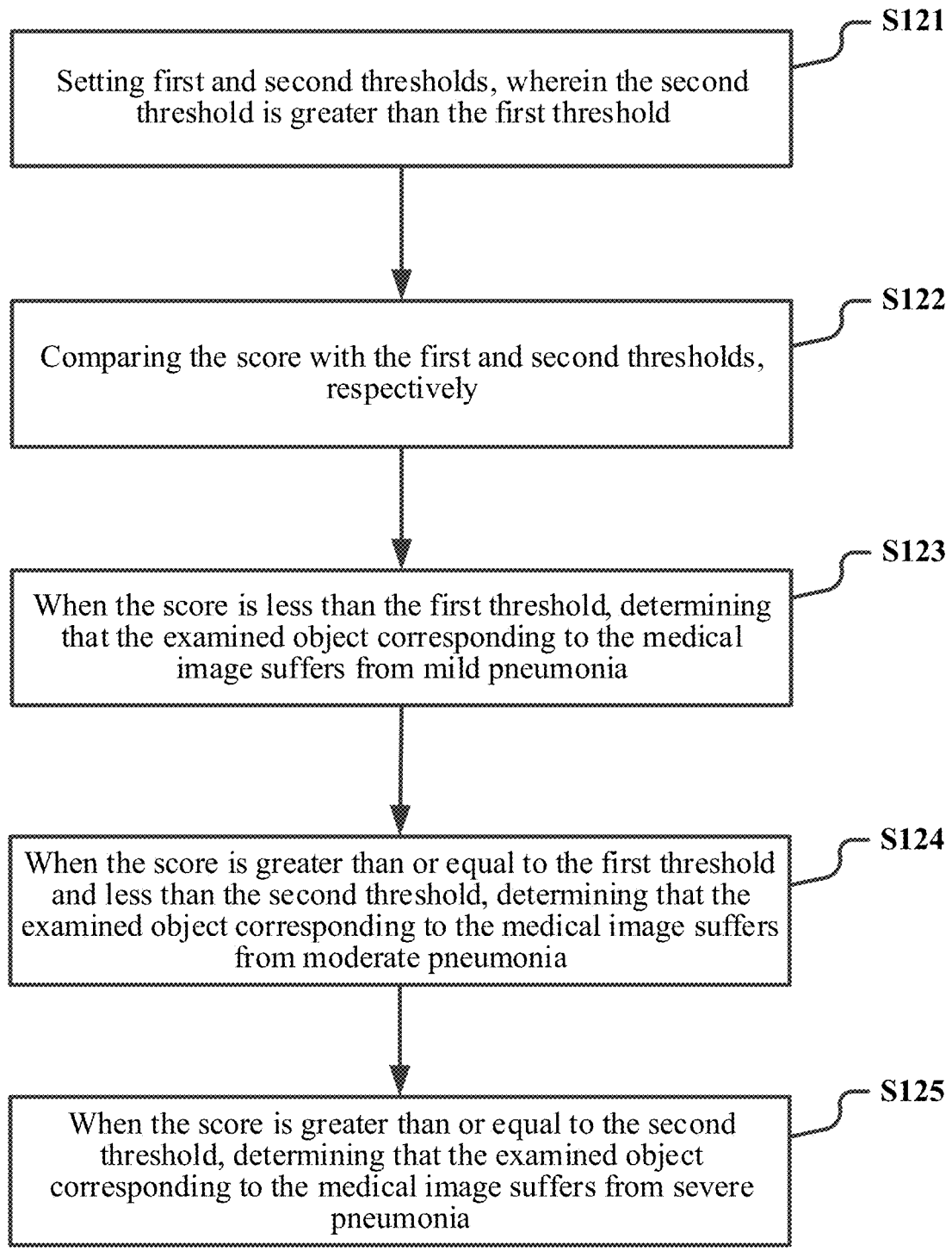
FIG. 12 is a flowchart of a diagnostic information evaluation method based on a medical image in an embodiment of the present invention.

In one embodiment, as shown in FIG. 12, step S84 may be implemented as the following steps S121-S125.

In step S121, first and second thresholds are set, where the second threshold is greater than the first threshold.

In step S122, the score is compared with the first and second thresholds, respectively.

In step S123, when the score is less than the first threshold, it is determined that the examined object corresponding to the medical image suffers from mild pneumonia.

In step S124, when the score is greater than or equal to the first threshold and less than the second threshold, it is determined that the examined object corresponding to the medical image suffers from moderate pneumonia.

In step S125, when the score is greater than or equal to the second threshold, it is determined that the examined object corresponding to the medical image suffers from severe pneumonia.

In this embodiment, the first and second thresholds are set, where the second threshold is greater than the first threshold; the score is compared with the first and second thresholds, respectively; when the score is less than the first threshold, it is determined that the examined object corresponding to the medical image suffers from mild pneumonia; when the score is greater than or equal to the first threshold and less than the second threshold, it is determined that the examined object corresponding to the medical image suffers from moderate pneumonia; when the score is greater than or equal to the second threshold, it is determined that the examined object corresponding to the medical image suffers from severe pneumonia.

This embodiment has the following beneficial effects: by setting threshold intervals related to the scores, evaluation of the severity of the pneumonia the patient currently suffers from can be realized.

It should be noted that, in the present application, the evaluation of the severity of the pneumonia can also be realized in other manner, for example:

setting first, second and third score intervals, where the maximum value of the first score interval is less than or equal to the minimum value of the second score interval, and the maximum value of the second score interval is less than or equal to the minimum value of the third score interval; determining the score interval to which a score belongs; determining, according to the score interval to which the score belongs, the severity of the pneumonia of the examined object corresponding to the medical image, where pneumonia is divided into mild pneumonia, moderate pneumonia and severe pneumonia according to the severity; when the score interval to which the score belongs is the first score interval, determining that the examined object corresponding to the medical image suffers from mild pneumonia; when the score interval to which the score belongs is the second score interval, determining that the examined object corresponding to the medical image suffers from moderate pneumonia; and when the score interval to which the score belongs is the third score interval, determining that the examined object corresponding to the medical image suffers from severe pneumonia.

Figure 13:
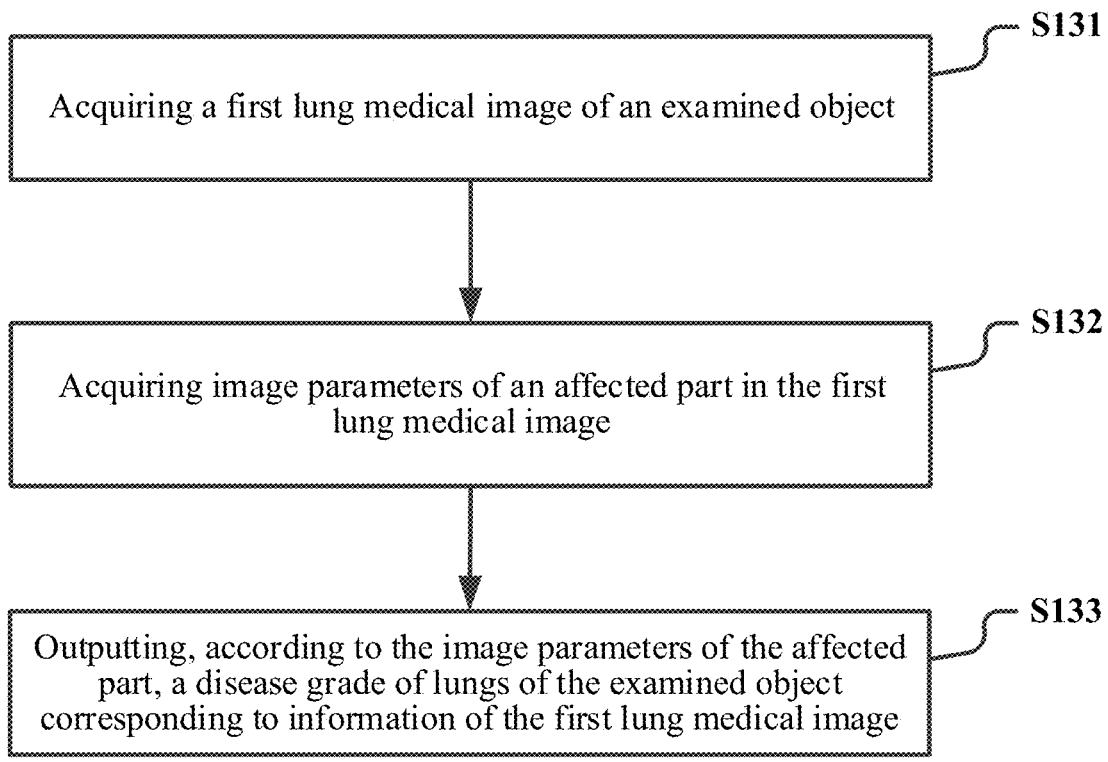
FIG. 13 is a flowchart of a diagnostic information evaluation method based on a medical image in an embodiment of the present invention.

FIG. 13 is a flowchart of a diagnostic information evaluation method based on a medical image in an embodiment of the present invention. As shown in FIG. 13, the method may be implemented as the following steps S131-S133.

In step S131, a first lung medical image of an examined object is acquired.

In step S132, image parameters of an affected part in the first lung medical image are acquired.

In step S133, a disease grade of lungs of the examined object corresponding to information of the first lung medical image is output according to the image parameters of the affected part.

It should be understood that the interaction method of the embodiments involved in the present disclosure may be based on the necessary diagnostic information processing method, and includes determining the disease grade of the lungs of the examined object corresponding to the corresponding information of the first lung medical image.

It should be noted here that the first lung medical image involved in this embodiment may be the medical image involved in the foregoing embodiments.

Figure 14:
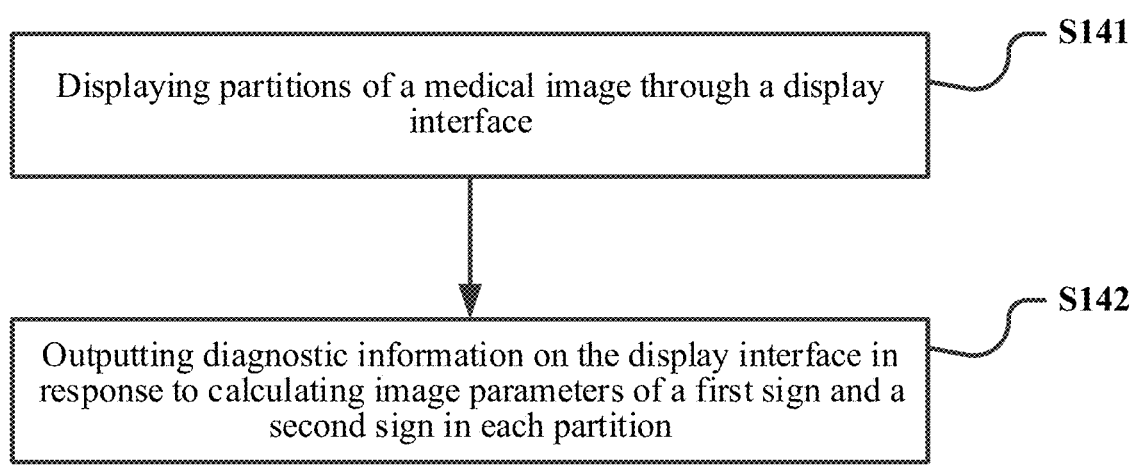
FIG. 14 is a flowchart of a diagnostic information display method based on a medical image in an embodiment of the present invention.

In combination with the foregoing diagnostic information evaluation methods based on a medical image, the present application further discloses a diagnostic information display method based on a medical image. FIG. 14 is a flowchart of a diagnostic information display method based on a medical image in an embodiment of the present invention. As shown in FIG. 14, the method may be implemented as the following steps S141-S142.

In step S141, partitions of a medical image are displayed through a display interface.

In step S142, diagnostic information is output on the display interface in response to calculating image parameters of a first sign and a second sign in each partition.

The diagnostic information includes at least one of:

volume proportions of the first sign and the second sign, scores obtained based on volumes of the first sign and the second sign, or an evaluation result of the medical image obtained based on the scores.

Figure 15:
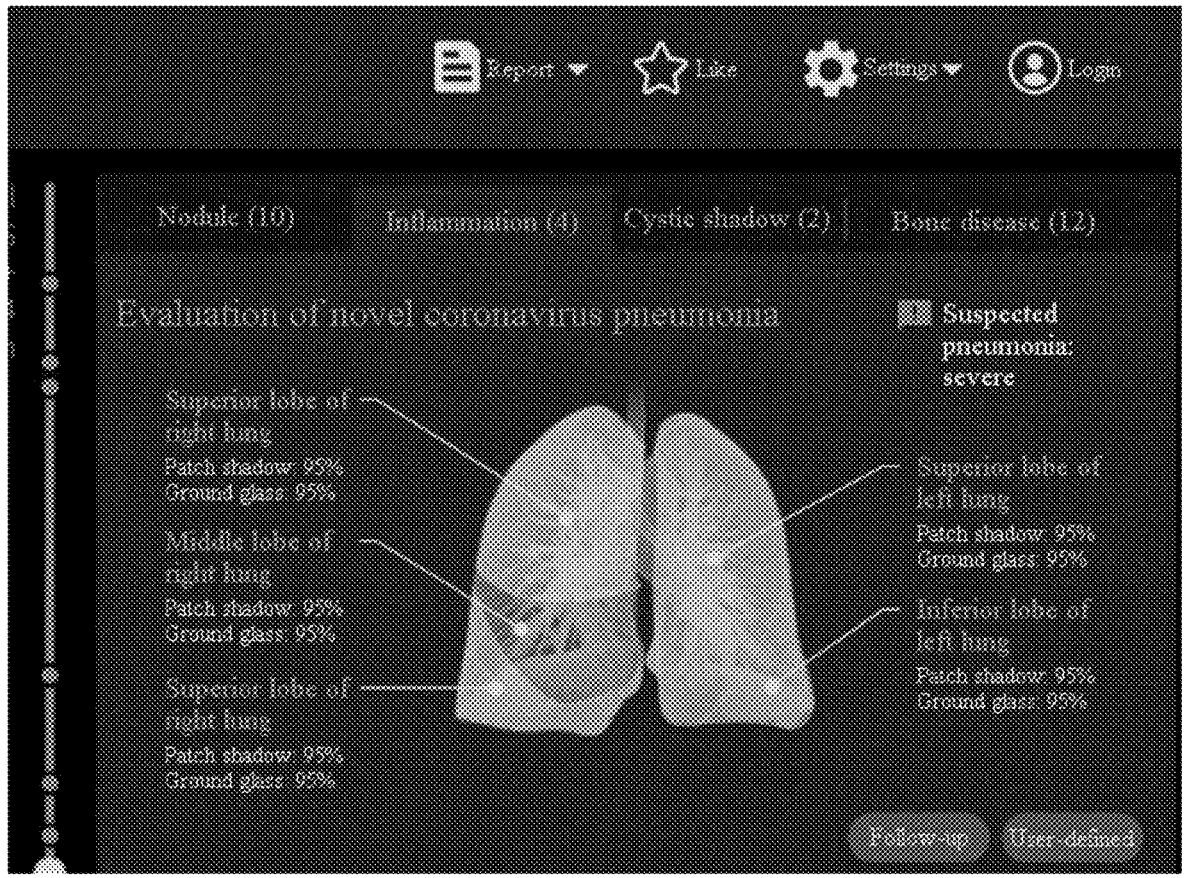
FIG. 15 shows a novel coronavirus pneumonia evaluation interface.

When the medical image is a lung medical image, as shown in FIG. 15, the partitions of the lung medical image are displayed through the display interface. FIG. 15 is applicable to the case mentioned in the foregoing embodiments where the region of interest (i.e., the lungs) in the medical image are divided into five partitions. In response to calculating the image parameters of the first sign and the second sign in each partition, at least one piece of the following diagnostic information is output on the display interface: the volume proportions of the first sign and the second sign, the scores obtained based on the volumes of the first sign and the second sign, or the evaluation result of the medical image obtained based on the scores.

This embodiment provides a diagnostic information display method based on a medical image which is disclosed in combination with the foregoing diagnostic information evaluation methods based on a medical image. Therefore, it is not difficult to understand that the medical image involved in this embodiment may be the medical image involved in the foregoing embodiments, and the partitions involved in this embodiment can also be determined through the partitioning mode described in the embodiments corresponding to the foregoing diagnostic information evaluation methods based on a medical image. The first sign involved in this embodiment may be a patch region, and the second sign may be a ground glass region.

Furthermore, the volume proportions of the first sign and the second sign, the scores obtained based on the volumes of the first sign and the second sign, and the evaluation result of the medical image obtained based on the scores can all be obtained through the solutions described in the embodiments corresponding to the foregoing diagnostic information evaluation methods based on a medical image.

From the descriptions of the foregoing embodiments, it can be known that the first lung medical image in the foregoing embodiments may be the first target CT image involved in the foregoing embodiments. In addition, from the foregoing descriptions "the second lung medical image of an examined object is acquired. The second lung medical image and the first lung medical image in the foregoing embodiments are lung medical images of the same examined object in different periods" and "the second data is CT value density data of a region of interest in a second target CT image obtained at different time from the first target CT image", it is not difficult to see that the second lung medical image may also be the second target CT image.

In addition, the first lung medical image, the second lung medical image, the first target CT image, and the second target CT image are only different in the generation time, and the first lung medical image may also be a medical image. Therefore, it is not difficult to understand that the medical images may also be the first lung medical image, the second lung medical image, the first target CT image, and the second target CT image.

In addition, it can also be seen from FIG. 3D and FIG. 6 that, the embodiment relating to "multiple lung medical images are rendered with multiple colors, where portions of the rendered lung medical images having different CT values and/or CT value ranges correspond to different colors; and multiple rendered lung medical images are output" corresponds to the embodiment relating to "a first graph is formed based on first data, where the first graph is represented by a first color, and the first data is CT value density data of a region of interest in a first target CT image; a second graph is formed based on second data, where the second graph is represented by a second color; and "an overlapping portion of the first graph and the second graph is determined, and the overlapping portion is represented by a third color". For example, the CT values may include the CT value density data, and the content "portions of the rendered lung medical images having different CT values and/or CT value ranges correspond to different colors" corresponds to the content "the first graph is represented by a first color, the second graph is represented by a second color, and the overlapping portion is represented by a third color".

Thus, on this basis, it is not difficult to see that the embodiments corresponding to the multiple methods involved in the above-mentioned solutions (such as a diagnostic information processing method based on a medical image, a method for displaying a diagnostic information interface, a diagnostic information interaction method based on a medical image, a diagnostic information evaluation method based on a medical image, and a diagnostic information display method based on a medical image) can be mutually referred to, used for reference and implemented in combination. On this basis, the present application provides a solution that combines the above-mentioned embodiments for implementation, and the details are as follows.

Figure 16:
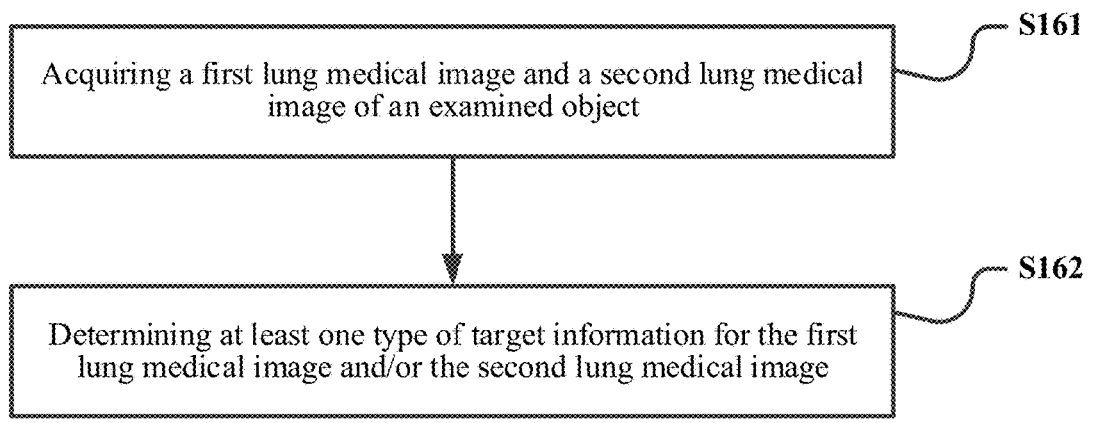
FIG. 16 is a flowchart corresponding to a general embodiment in an embodiment of the present invention.

FIG. 16 is a flowchart corresponding to a general embodiment in an embodiment of the present invention. The method may be implemented as the following steps S161-S162.

In step S161, a first lung medical image and a second lung medical image of an examined object are acquired, where the first lung medical image and the second lung medical image are lung medical images obtained from the same examined object at different time.

In step S162, for the first lung medical image and/or the second lung medical image, at least one type of the following target information is determined:

a disease grade of lungs of the examined object, probability distribution of CT values in the lung medical images at different time, disease evaluation results of regions of interest in the lung medical images, development trend information, and a disease development speed.

In one embodiment, the disease grade of the examined object is determined by:

acquiring image parameters of an affected part in the first lung medical image; and determining, according to the image parameters of the affected part, a disease grade of lungs of the examined object corresponding to information of the first lung medical image.

In one embodiment, the probability distribution of the CT values in the lung medical images at different time is determined by:

acquiring CT density data of regions of interest in the first lung medical image and the second lung medical image;

generating, based on the CT density data, a first graph corresponding to the first lung medical image and a second graph corresponding to the second lung medical image; and putting the first graph and the second graph in the same coordinate system to form a comparison diagram of the probability distribution of the CT values in the lung medical images at different time, where the first graph is represented by a first color, the second graph is represented by a second color, and an overlapping portion of the first graph and the second graph is represented by a third color.

In one embodiment, the disease evaluation results of the regions of interest are determined by:

partitioning the region of interest in the first lung medical image and/or the second lung medical image to obtain at least N partitions, where N is a natural number greater than or equal to 2;

calculating at least a volume of a first sign and a volume proportion of a second sign in each partition;

acquiring score values corresponding to the volume proportions of the first sign and the second sign, and acquiring a score of each partition based on the score values; and evaluating the region of interest according to the score of each partition.

The evaluating the region of interest according to the score of each partition includes: setting a corresponding score threshold, and then determining, based on the score threshold, the severity of a disease of an examined object corresponding to the medical image.

The specific implementations of the following steps involved in this general embodiment are all described in the foregoing embodiments, and therefore, it is only necessary to make reference to the foregoing embodiments, and no repeated description is made here:

determining disease development trend information of the examined object, where different development trends (a first development trend or a second development trend) correspond to different diagnostic results; calculating a disease development speed of the examined object based on the generation time of the first lung medical image and the second lung medical image and a volume change trend of an affected part; and acquiring volumes of the affected parts in the first lung medical image and the second lung medical image and the structure of a neuron network through the neuron network.

It is not difficult to understand that the disease grade can only be used to determine the severity of the disease, but cannot be used to determine whether the disease is developing in a good direction or a worse direction, or to determine when the disease can be cured, or when the disease will progress to the next disease grade, excluding external influences. Therefore, a lot of information is required to be integrated to make more accurate predictions about "whether the disease is developing in a good direction or a worse direction", "when the disease can be cured, or when the disease will progress to the next disease grade", etc.

Therefore, through the above-mentioned solution, different types of target information can be obtained, such as the disease grade, the probability distribution of CT values in lung medical images at different time, the disease evaluation results of the regions of interest in the lung medical images, and disease development trend information. Hence, various conditions of the lung disease of the examined object can be determined from multiple angles, which is beneficial to the diagnosis of various lung diseases (such as novel coronavirus pneumonia), thereby providing richer materials and diagnostic basis, and helping physicians or diagnostic equipment to diagnose diseases more accurately.

In the present application, when there are multiple types of target information, the conditions of the disease can be comprehensively determined through the multiple types of target information.

For example, disease grades are divided into grade 1, grade 2, grade 3 and grade 4 according to the severity from mild to severe. Assuming that the target information is a disease grade and a disease development trend, the current disease grade is determined to be 2 according to the current medical image, and the volume of the affected part is determined to be decreasing according to the disease development trend, it can be predicted that the disease will progress to grade 1 in the future.

For another example, if the target information is a disease grade, a disease development trend and a disease development speed, the current disease grade is determined to be 2 according to the current medical image, and the volume of the affected part is determined to be decreasing according to the disease development trend, when the disease will return to grade 1 can be predicted in combination with the disease development speed. Thus, a more comprehensive judgment result can be obtained.

It can be understood that the above are only examples, which are used to describe the contents of the present invention more clearly, and the solutions for comprehensively determining disease situations are not limited to the foregoing two examples.

Those skilled in the art should understand that the embodiments of the present invention can be provided as a method, a system, or a computer program product. Therefore, the present invention may be embodied in the form of complete hardware embodiments, complete software embodiments, or embodiments combining software and hardware. Moreover, the present invention may use the form of a computer program product implemented on one or more computer-usable storage media (including, but not limited to, disk storage, optical storage, etc.) containing computer-usable program codes.

The present invention is described with reference to flowcharts and/or block diagrams of a method, a device (system), and a computer program product according to the embodiments of the present invention. It should be understood that each step and/or box in a flowchart and/or a box diagram and the combination of steps and/or boxes in the flowchart and/or box diagram can be implemented by computer program instructions. These computer program instructions can be provided to a processor of a general-purpose computer, a special-purpose computer, an embedded processor, or another programmable data processing device to produce a machine, so that an apparatus for implementing functions specified in one or more steps in the flowchart and/or one or more boxes in the box diagram can be produced through the instructions executed by the processor of the computer or another programmable data processing device.

These computer program instructions can also be stored in a computer readable memory that can guide a computer or another programmable data processing device to operate in a particular manner, such that the instructions stored in the computer readable memory produce a product including an instruction apparatus, and the instruction apparatus implements the functions specified in one or more steps in the flowchart and/or one or more boxes in the box diagram.

These computer program instructions can also be loaded on a computer or another programmable data processing device to enable the computer or another programmable device to execute a series of operation steps to perform computer-implemented processing, such that the instructions executed on the computer or another programmable device provide steps for implementing the functions specified in one or more steps in the flowchart and/or one or more boxes in the box diagram.

Apparently, those skilled in the art can make various modifications and changes to the present invention without departing from the spirit and scope of the present invention. In this way, if these modifications and changes of the present invention fall within the scope of the claims of the present invention and their equivalent technologies, the present invention is also intended to include these modifications and changes.

The invention claimed is:

1. A diagnostic information processing method based on a medical image, comprising the steps of:
   acquiring a first lung medical image of an examined object;
   acquiring image parameters of an affected part in the first lung medical image; which comprises the step of: inputting at least one first lung medical image into a neuron network to determine a volume of the affected part in the first lung medical image; and
   determining, according to the image parameters of the affected part, a disease grade of lungs of the examined object corresponding to information of the first lung medical image,
   wherein the neuron network comprises:
   a first detection model configured to detect a candidate patch shadow, a cutting model, a second detection model configured to detect a patch shadow interval, and a volume calculation model configured to calculate the volume of the affected part; and
   the step of inputting at least one first lung medical image into a neuron network to determine a volume of the affected part in the first lung medical image comprises the steps of:
   passing the at least one first lung medical image through N consecutive convolution feature extraction modules in the first detection model, so that the N consecutive convolution feature extraction modules obtain image features of a patch shadow in the first lung medical image, wherein N is a positive integer;
   inputting image features of the affected part in the first lung medical image into a fully connected layer in the first detection model, so that the fully connected layer outputs the candidate patch shadow based on the image features;
   passing the candidate patch shadow through the cutting model, so that the cutting model cuts the candidate patch shadow in different directions in space multiple times to obtain multiple section images of the candidate patch shadow in multiple directions in space;
   passing multiple consecutive section images through M consecutive convolution feature extraction modules in the second detection model, so that the M consecutive convolution feature extraction modules obtain image features of the section images, wherein M is a positive integer;
   inputting the image features of the section images into a fully connected layer in the second detection model, so that the fully connected layer outputs patch shadow information based on the image features; and passing the patch shadow information through the volume calculation model, so that the volume calculation model calculates the volume of the affected part in the first lung medical image.

2. The method according to claim 1, wherein the determining, according to the image parameters of the affected part, a disease grade of lungs of the examined object corresponding to information of the first lung medical image comprises:

comparing a volume of the affected part with a target relationship table, wherein the target relationship table stores a corresponding relationship between the volume of the affected part and the disease grade; and determining the disease grade of the lungs of the examined object according to a comparison result.

3. The method according to claim 1, wherein the determining, according to the image parameters of the affected part, a disease grade of lungs of the examined object corresponding to first lung medical image information comprises:

calculating a volume proportion of the affected part in the lungs; and inputting a volume of the affected part and the volume proportion of the affected part in the lungs into a disease grade calculation model, to obtain the disease grade of the lungs of the examined object that is comprehensively calculated by the disease grade calculation module based on the volume of the affected part and the volume proportion of the affected part in the lungs.

4. The method according to claim 1, further comprising:

acquiring a second lung medical image of the examined object;

acquiring a volume of an affected part in the second lung medical image;

comparing the volume of the affected part in the second lung medical image with the volume of the affected part in the first lung medical image to determine a volume change trend of the affected part; and determining development trend information of a lung disease of the examined object according to the volume change trend of the affected part.

5. The method according to claim 4, wherein determining a development trend of the lung disease of the examined object according to the volume change trend of the affected part comprises:

when the volume of the affected part conforms to a first trend, determining a first diagnostic result of the examined object; and when the volume of the affected part conforms to a second trend, determining a second diagnostic result of the examined object.

6. The method according to claim 4, further comprising:

acquiring generation time of the first lung medical image and the second lung medical image; and calculating a disease development speed of the examined object according to the generation time and the volume change trend of the affected part.

7. The method according to claim 1, further comprising:

rendering the first lung medical image based on a single color to generate a third lung medical image, wherein a color depth after rendering is positively correlated with a CT (Computed Tomography) value; and/or rendering the first lung medical image based on multiple colors to generate a fourth lung medical image, wherein different CT values are rendered with different types of colors; and outputting the first lung medical image, the third lung medical image and/or the fourth lung medical image.

8. The method according to claim 1, further comprising:

rendering multiple lung medical images with multiple colors, wherein portions of the rendered lung medical images having different CT (Computed Tomography) values and/or CT value ranges correspond to different colors; and outputting multiple rendered lung medical images.

9. A non-transitory readable storage medium, wherein instructions in the storage medium, when executed by a processor in a device, enable the device to execute the method according to claim 1.

* * * * *